United States Patent
Konopa et al.

(10) Patent No.: US 10,202,349 B2
(45) Date of Patent: Feb. 12, 2019

(54) ASYMMETRIC BIS-ACRIDINES WITH ANTITUMOUR ACTIVITY AND THEIR USES

(71) Applicant: POLITECHNIKA GDAŃSKA, Gdańsk (PL)

(72) Inventors: Jerzy Kazimierz Konopa, Gdansk (PL); Barbara Horowska, Gdansk (PL); Ewa Maria Paluszkiewicz, Pruszcz Gdanski (PL); Barbara Borowa-Mazgaj, Godkowo (PL); Ewa Anna Augustin, Gdansk (PL); Anna Skwarska, Nidzica (PL); Zofia Mazerska, Gdansk (PL)

(73) Assignee: Gdansk University of Technology, Gdansk (PL)

( * ) Notice: Subject to any disclaimer, the term of this patent is extended or adjusted under 35 U.S.C. 154(b) by 0 days.

(21) Appl. No.: 15/559,812

(22) PCT Filed: Mar. 17, 2016

(86) PCT No.: PCT/EP2016/055743
§ 371 (c)(1),
(2) Date: Sep. 19, 2017

(87) PCT Pub. No.: WO2016/150799
PCT Pub. Date: Sep. 29, 2016

(65) Prior Publication Data
US 2018/0086712 A1    Mar. 29, 2018

(30) Foreign Application Priority Data
Mar. 20, 2015   (EP) .................................... 15461518

(51) Int. Cl.
*C07D 219/12* (2006.01)
*A61K 31/473* (2006.01)
*A61P 35/00* (2006.01)
*C07D 219/10* (2006.01)

(52) U.S. Cl.
CPC .......... *C07D 219/10* (2013.01); *A61K 31/473* (2013.01); *A61P 35/00* (2018.01); *C07D 219/12* (2013.01)

(58) Field of Classification Search
CPC .......................... C07D 219/12; A61K 31/473

USPC .................................. 546/106, 107; 514/297
See application file for complete search history.

(56) References Cited

U.S. PATENT DOCUMENTS

| 5,231,100 A * | 7/1993 | Cholody ............... C07D 471/06 514/288 |
| 5,508,289 A * | 4/1996 | Michejda ............ A61K 49/0026 514/287 |
| 5,886,185 A | 3/1999 | Chou et al. |
| 6,187,775 B1 * | 2/2001 | Michejda ............... C07D 471/06 514/253.02 |
| 2002/0099211 A1 * | 7/2002 | Konopa ............... C07D 219/06 546/105 |

FOREIGN PATENT DOCUMENTS

| CN | 104 230 805 A | 12/2014 |
| EP | 0 038 572 A1 | 10/1981 |
| WO | 98/57956 A1 | 12/1998 |
| WO | 99/06372 A1 | 2/1999 |
| WO | 2011/051950 A1 | 5/2011 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Humcha K Hariprakasha et al., "Optimization of Naphthalimide-imidazoacridone with Potent Antitumor Activity Leading to Clinical Candidate (HKH40A, RTA 502)", American Chemical Society, Journal of Medicinal Chemistry, 2007, vol. 50, No. 23, p. 5557-5560.
International Search Authority/EPO, International Search Report dated Jun. 1, 2016 in International Patent Application No. PCT/EP2016/055743, 3 pages.

* cited by examiner

*Primary Examiner* — Venkataraman Balasubramanian
(74) *Attorney, Agent, or Firm* — Masuvalley & Partners

(57) ABSTRACT

We disclose novel asymmetric bis-acridines with antitumor activity. These compounds are useful for use in pharmaceuticals, particularly in the treatment or the prevention of neoplasms.

7 Claims, 1 Drawing Sheet

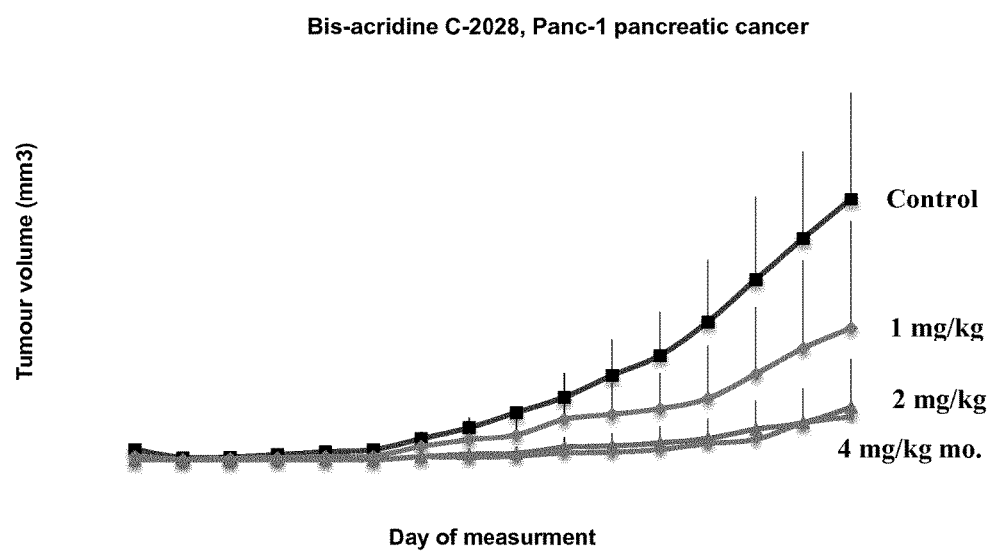
*The effect of bis-acridine C-2028 on the growth of the xenografted pancreatic tumour Panc-1 of human origin in mice lacking a thymus*

ASYMMETRIC BIS-ACRIDINES WITH ANTITUMOUR ACTIVITY AND THEIR USES

RELATED APPLICATIONS

This application is the U.S. National Phase application under 35 U.S.C. § 371 of International Patent Application No. PCT/EP2016/055743, filed on Mar. 17, 2016, which claims priority to European Patent Application No. 15461518.1, filed on Mar. 20, 2015, which are hereby expressly incorporated by reference in their entirety for all purposes.

The subject of the present invention are novel asymmetric bis-acridines with antitumour activity. These compounds are useful in pharmaceutics, particularly in the treatment or the prevention of neoplasms. There are dimers known from the state of the art, that are combinations (using an appropriate linker) of monomeric anti-neoplasmic compounds or their structural elements responsible for the anti-neoplasmic properties of said monomeric compounds [Cholody W. M. et al., Cancer Chemother., Pharmacol., 2001, 47, 241-249; Humcha K. et al., J. Med. Chem., 2007, 50, 5557-5560]. The goal of the present invention is to deliver novel compounds usable in oncology, particularly in the treatment of difficult to treat neoplasms, in particular pancreatic neoplasms.

Unexpectedly, this goal has been attained by the present invention.

The subject of the present invention is a compound defined by the formula:

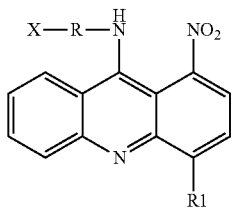

where: R denotes a group selected from among: $(CH_2)_nNH(CH_2)_n$, $(CH_2)_nNCH_3(CH_2)_n$, $(CH_2)_n$piperazinyl(1,4)$(CH_2)$ or $(CH_2)_nNH(CH_2)_nNH(CH_2)_n$, among which n is an integer from 2 to 4, R1 denotes H or $CH_3$, X denotes the group selected from among:

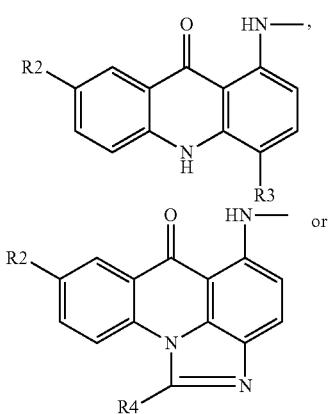

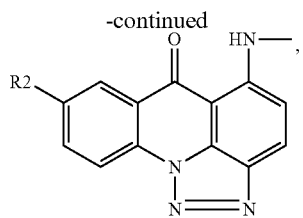

among which: R2 denotes H, OH or $OCH_3$, R3 denotes H, $NO_2$ or $CH_3$, a R4 denotes H or $CH_3$, or a pharmaceutically admissible salt thereof, in particular hydrochloride or methanesulphonate.

Preferably, X denotes the group:

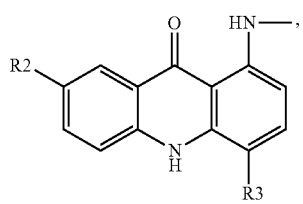

wherein it is selected from among the following compounds: 9-{N-[(7-hydroxy-4-nitro-9(10H)acridono-1-yl)aminopropyl]-N-methylaminopropylamino}-1'-nitroacridonex2HCl, 1-[3-(7-hydroxy-4-nitro-9 (10H)-acridono-1-yl)aminopropyl]-4-3'-[(1'-nitroacridin-1-yl)-aminopropyl]piperazinex3 HCl, 9-{N-[(4-methyl-9(10H)-acridono-1-yl)aminoethyl]ethylamino}-1'-nitroacridinex3 HCl, 1-[3-(4-methyl-9(10H)-acridono-1-yl)aminopropyl]-4-3'-[(1'-nitroacridin-1-yl)-aminopropyl]piperazinex4HCl, 9-[N-(4-methyl-9(10H) acridono-1-yl)-aminoethylaminoethylamino-ethylamino]-1'-nitroacridinex4HCl, 9-{N-[(4-methyl-9(10H)-acridono-1-yl)aminoethyl]ethylamino}-4'-methyl-1'-nitroacridinex 2CH$_3$SO$_2$OH, —[3-(4-methyl-9(10H)-acridono-1-yl) aminopropyl]-4-[3'-(4'-methyl-1'-nitroacridin-1-yl)-aminopropyl]piperazinex3CH$_3$SO$_2$OH, 9-{N-[(7-hydroxy-4-nitro-9(10H)acridono-1-yl)aminopropyl]-N-methylaminopropylamino}-4'-methyl-1'-nitroacridinex 2HCl, 1-[3-(7-hydroxy-4-nitro-9(10H)-acridono-1-yl) aminopropyl]-4-[3'-(4'-methyl-1'-nitro-acridin-1-yl)-aminopropyl]piperazinex3HCl, 9-{N-[(7-hydroxy-4-nitro-9 (10H)acridono-1-yl)aminopropyl]-aminopropylamino}-4'-methyl-1'-nitroacridinex2HCl, 9-{N-[(4-methyl-9(10H)-acridono-1-yl)aminopropyl]propylamino}-4'-methyl-1'-nitroacridinex3HCl, 9-{N-[(4-methyl-9(10H)-acridono-1-yl)aminopropyl]-N-methylaminopropylamino}-4'-methyl-1'-nitroacridinex3HCl, 9-[N-(4-methyl-9(10H)-acridono-1-yl)-aminoethylaminoethylamino-ethylamino]-4'-methyl-1'-nitroacridinx4HCl, 9-{N-[(4-nitro-9(10H)-acridono-1-yl) aminopropyl]-N-methylaminopropylamino}-1'-nitroacridinex2HCl, 9-{N-[(4-nitro-9(10H)acridono-1-yl) aminopropyl]-N-methylaminopropylamino}-4'-methyl-1'-nitroacridinex2HCl, 1-[3-(4-nitro-9(10H)-acridono-1-yl) aminopropyl]-4-[3'-(4'-methyl-1'-nitroacridin-1-yl)-aminopropyl]piperazinex3HCl, 1-[3-(4-nitro-9(10H)-acridono-1-yl)aminopropyl]-4-[3'-(1'-nitroacridin-1-yl)-aminopropyl]piperazinex3HCl, 9-[N-(4-nitro-9(10H) acridono-1-yl)-aminoethylaminoethylamino-ethylamino]-4'-methyl-1'-nitroacridinex3HCl, 9-[N-(4-nitro-9(10H) acridono-1-yl)-aminoethylaminoethylamino-ethylamino]-1'-nitroacridinex3HCl, 9-{N-[(4-methyl-9(10H)-acridono-1-yl)aminopropyl]propylamino}-1'-nitroacridinex3HCl, 9-[N-(4-nitro-9(10H)acridono-1-yl)-aminopropylaminoethylamino-propylamino]-4'-methyl-1'-nitroacridine×3HCl,
9-[N-(4-nitro-9(10H)acridono-1-yl)-aminopropylaminoethylamino-propylamino]-1'-nitroacridine×3HCl.
Equally preferably, X denotes the group:

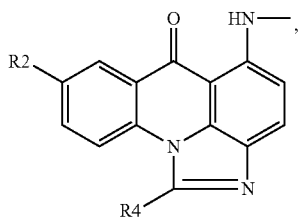

wherein it is selected from among the following compounds: 1-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-imidazo[4,5,1-de]-acridin-6-on-5-yl)aminopropyl]-4-[3'-(1'-nitroacridin-1-yl)-aminopropyl]piperazine×3HCl, 9-{N-[(imidazo[4,5,1-de]-acridin-6-on-5-yl)aminopropyl]-N-methylaminopropylamino}-1'-nitroacridine×1.5HCl, 9-[N-(imidazo[4,5,1-de]-acridin-6-on)-aminoethylaminoethylamino-ethylamino]-4'-methyl-1'-nitroacridine×4HCl, 1-[3-(imidazo[4,5,1-de]-acridin-6-on-5-yl)aminopropyl]-4-[3'-(1'-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-1'-nitroacridine×3HCl, 9-{N-[(8-hydroxyimidazo[4,5,1-de]-acridin-6-on-5-yl)aminopropyl]-N-methylaminopropylamino}-4'-methyl-1'-nitroacridine×3HCl, 1-[3-(8-methoxy-imidazo[4,5,1-de]-acridin-6-on-5-yl)aminopropyl]-4-[3'-(1'-nitroacridin-1-yl)-aminopropyl]piperazine×4HCl, 1-[3-(imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl, 9-{N-[(imidazo[4,5,1-de]-acridin-6-on-5-yl)aminopropyl]-N-methylaminopropylamino}-4'-methyl-1'-nitroacridine×3HCl.
Equally preferably, X denotes the group:

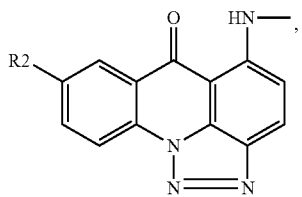

wherein it is selected from among the following compounds: 1-[3-(8-hydroxy-6H-[1,2,3]triazolo[4,5,1-de]-acridin-6-on-5-yl)aminopropyl]-4-[3'-(1'-nitroacridin-1-yl)-aminopropyl]piperazine×4HCl, 1-[3-(6H-[1,2,3]triazolo[4,5,1-de]-acridin-6-on-5-yl)aminopropyl]-4-[3'-(1'-nitroacridin-1-yl)-aminopropyl]piperazine×4HCl, 9-{N-[(8-hydroxy-6H-[1,2,3]triazolo[4,5,1-de]-acridin-6-on-5-yl)aminopropyl]-N-methylaminopropylamino}-1'-nitroacridine×2CH₃SO₂OH, 9-{N-5-[(8-hydroxy-6H-[1,2,3]triazolo[4,5,1-de]-acridin-6-on-5-yl)aminopropyl]-N-methylaminopropylamino}-4'-methyl-1'-nitroacridine×3HCl, 1-[3-(8-hydroxy-6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl, 1-[3-(6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl, 9-{N-5-[(6H-[1,2,3]triazolo[4,5,1-de]-acridin-6-on-5-yl)aminopropyl]-N-methylaminopropylamino}-1'-nitroacridine×3HCl, 9-{N-5-[(6H-[1,2,3]triazolo[4,5,1-de]-acridin-6-on-5-yl)aminopropyl]-N-methylaminopropylamino}-4'-methyl-1'-nitroacridine×3HCl, 9-{N-5-[(6H-[1,2,3]triazolo[4,5,1-de]-acridin-6-on-5-yl)aminopropyl]-aminopropylamino}-4'-methyl-1'-nitroacridine×3HCl, 9-{N-5-[(6H-[1,2,3]triazolo[4,5,1-de]-acridin-6-on-5-yl)aminopropyl]-aminopropylamino}-1'-nitroacridine×3HCl. The next subject of the present invention is a compound according to the present invention defined above for use in pharmaceuticals. The next subject of the present invention is a compound according to the present invention defined above for use in the treatment and prevention of neoplasms. Preferably, the neoplasm is a pancreatic tumour, and the compound is selected from among the following compounds: 1-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-imidazo[4,5,1-de]-acridin-6-on-5-yl)aminopropyl]-4-[3'-(1'-nitroacridin-1-yl)-aminopropyl]piperazine×3HCl, 9-{N-[(imidazo[4,5,1-de]-acridin-6-on-5-yl)aminopropyl]-N-methylaminopropylamino}-1'-nitroacridine×1.5HCl, 9-[N-(imidazo[4,5,1-de]-acridin-6-on)-aminoethylaminoethylamino-ethylamino]-4'-methyl-1'-nitroacridine×4HCl, 1-[3-(imidazo[4,5,1-de]-acridin-6-on-5-yl)aminopropyl]-4-[3'-(1'-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-1'-nitroacridine×3HCl, 9-{N-[(8-hydroxyimidazo[4,5,1-de]-acridin-6-on-5-yl)aminopropyl]-N-methylaminopropylamino}-4'-methyl-1'-nitroacridine×3HCl, 1-[3-(8-methoxy-imidazo[4,5,1-de]-acridin-6-on-5-yl)aminopropyl]-4-[3'-(1'-nitroacridin-1-yl)-aminopropyl]piperazine×4HCl, 1-[3-(imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl, 9-{N-[(imidazo[4,5,1-de]-acridin-6-on-5-yl)aminopropyl]-N-methylaminopropylamino}-4'-methyl-1'-nitroacridine×3HCl, in particular a compound selected from among: C-2041 1-[3-(imidazo[4,5,1-de]-acridin-6-on-5-yl)aminopropyl]-4-[3'-(1'-nitroacridin-1-yl)-aminopropyl]piperazine×4HCl, C-2045 9-{N-[(8-hydroxyimidazo[4,5,1-de]-acridin-6-on-5-yl)aminopropyl]-N-methylaminopropylamino}-4'-methyl-1'-nitroacridine× 3HCl, C-2053 9-{N-[(imidazo[4,5,1-de]-acridin-6-on-5-yl)aminopropyl]-N-methylaminopropylamino}-4'-methyl-1'-nitroacridine×3HCl, C-2028 9-{N-[(imidazo[4,5,1-de]-acridin-6-on-5-yl)aminopropyl]-N-methylaminopropylamino}-1'-nitroacridine×1.5HCl, particularly preferably C-2028 9-{N-[(imidazo[4,5,1-de]-acridin-6-on-5-yl)aminopropyl]-N-methylaminopropylamino}-1'-nitroacridine×1.5HCl.

The disclosed compounds are a completely novel group of acridine derivative. To date, no one has obtained asymmetric bis-acridines. We conducted a synthesis of such asymmetric bis-acridines by binding together, via linker chains, substantial structural elements of 1-nitroacridines, imidazoacridones and triazoloacridones. These elements are acridine cores devoided of a side chain, which likely also plays an important role in biological activity. Also used were acridones that are substrates in the synthesis of imidazo and triazoloacridones, that also exhibit anti-neoplasmic properties.

Three subgroups of compounds was obtained of novel asymmetric bis-acridines: 1. acridono-1-nitroacridine; 2. imidazoacridono-1-nitroacridine; 3. triazoloacridono-1-nitroacridine, which are connected by the presence of 1-nitroacridine in every obtained bis-acridine. In the example embodiments, described jointly 43 bis-acridines, for which, a broad spectrum of biological activity tests were performed, in particular anti-neoplasmic activity in vitro and in vivo against various types of neoplasms. All of the bis-acridines described in the examples possess their own laboratory codes as well as Roman numerals and letters, whereas substrates and intermediates are denoted with Arabic numerals and letters.

The first subgroup of example compounds according to the present invention consists of asymmetric dimers of acridono-1-nitroacridine (I a-x). These compounds, shown by the general formula I, we obtained using the method shown in schematic 1. The first stage was to obtain substrates used in later stages of the synthesis (compounds 1, 3). These are compounds described in literature (S. Archer, and in., *J. Am. Chem. Soc.*, 1954, 76 (2), 588-591; D. B. Capps, and In., *J. Med. Chem.*, 1992, 35, 4770-4778). Resynthesis was carried out of these derivative in 3-or 4-stage reactions based on literature data or using prior experience. For the synthesis of novel dimers (bis-acridines) (I), were used two derivative of 9-phenoxy-1-nitroacridine (3) and three derivative of 1-chloroacridone (1).

The next stage was to obtain monosubstituted derivatives of acridone with a side chain, with a terminal amino group (2)—12 derivatives. These compounds may be obtained using the method described in (W. M. Cholody, et al. in *J. Med. Chem.*, 1995, 38, 16, 3043-3052) or analogous methods. Derivatives of 1-chloroacridone were reacted with an excess of an appropriate aliphatic amines with good efficiency (depending on the synthesized derivatives: 60-95%). In the case of the presence of more than a single free amino group, the synthesis of a pure product necessitated the use of column chromatography. Obtained derivatives were condensed with the synthesized derivatives of 9-phenoxyacridine (3) in phenol yielding asymmetric dimers of (I), which were purified via crystallization and/or column chromatography. In some cases, it was necessary to clean the product a number of times using column chromatography in order to obtain compounds of a sufficient purity for biological testing.

Schematic 1. Synthesis of compounds defined by the structural formula I a-x

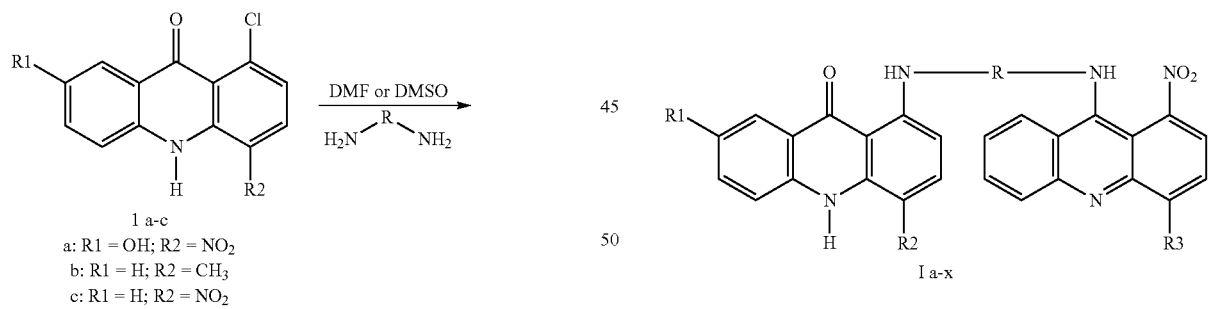

1 a-c
a: R1 = OH; R2 = NO$_2$
b: R1 = H; R2 = CH$_3$
c: R1 = H; R2 = NO$_2$ 2 a-1
a: R1 = OH; R2 = NO$_2$; R = (CH$_2$)$_3$NCH$_3$(CH$_2$)$_3$
b: R1 = OH; R2 = NO$_2$; R = (CH$_2$)$_3$piperazinyl(1,4)(CH$_2$)$_3$
c: R1 = H; R2 = CH$_3$; R = (CH$_2$)$_2$NH(CH$_2$)$_2$
d: R1 = H; R2 = CH$_3$; R = (CH$_2$)$_3$piperazinyl(1,4)(CH$_2$)$_3$
e: R1 = H; R2 = CH$_3$; R = (CH$_2$)$_2$NH(CH$_2$)$_2$NH(CH$_2$)$_2$
f: R1 = OH; R2 = NO$_2$; R = (CH$_2$)$_3$NH(CH$_2$)$_3$
g: R1 = H; R2 = CH$_3$; R = (CH$_2$)$_3$NH(CH$_2$)$_3$
h: R1 = H; R2 = CH$_3$; R = (CH$_2$)$_3$NCH$_3$(CH$_2$)$_3$
i: R$_1$ = H; R$_2$ = NO$_2$; R = (CH$_2$)$_3$NCH$_3$(CH$_2$)$_3$
j: R1 = H; R2 = NO$_2$; R = (CH$_2$)$_3$piperazinyl(1,4)(CH$_2$)$_3$
k: R1 = H; R2 = NO$_2$; R = (CH$_2$)$_2$NH(CH$_2$)$_2$NH(CH$_2$)$_2$
l: R$_1$ = H; R$_2$ = NO$_2$; R = (CH$_2$)$_3$NH(CH$_2$)$_2$NH(CH$_2$)$_3$ 3 a-b
a: R3 = H
b: R3 = CH$_3$ I a-x

TABLE 1

Example asymmetric dimers of acridono-1-nitroacridine (I a-x) obtained according to schematic 1.

| EXAMPLE | NO. | CODE | R1 | R2 | R | R3 |
| --- | --- | --- | --- | --- | --- | --- |
| 1 | Ia | C-1906 | OH | NO$_2$ | (CH$_2$)$_3$NCH$_3$(CH$_2$)$_3$ | H |
| 2 | Ib | C-1941 | OH | NO$_2$ | (CH$_2$)$_3$piperazinyl(1,4)(CH$_2$)$_3$ | H |
| 3 | Ic | C-1965 | H | CH$_3$ | (CH$_2$)$_2$NH(CH$_2$)$_2$ | H |
| 4 | Id | C-1973 | H | CH$_3$ | (CH$_2$)$_3$piperazinyl(1,4)(CH$_2$)$_3$ | H |
| 5 | Ie | C-1977 | H | CH$_3$ | (CH$_2$)$_2$NH(CH$_2$)$_2$NH(CH$_2$)$_2$ | H |
| 6 | If | C-2016 | H | CH$_3$ | (CH$_2$)$_2$NH(CH$_2$)$_2$ | CH$_3$ |
| 7 | Ig | C-2017 | H | CH$_3$ | (CH$_2$)$_3$piperazinyl(1,4)(CH$_2$)$_3$ | CH$_3$ |

TABLE 1-continued

Example asymmetric dimers of acridono-1-nitroacridine
(I a-x) obtained according to schematic 1.

| EXAMPLE | NO. | CODE | R1 | R2 | R | R3 |
|---|---|---|---|---|---|---|
| 8 | Ih | C-2019 | OH | $NO_2$ | $(CH_2)_3NCH_3(CH_2)_3$ | $CH_3$ |
| 9 | Ii | C-2020 | OH | $NO_2$ | $(CH_2)_3$piperazinyl$(1,4)(CH_2)_3$ | $CH_3$ |
| 10 | Ij | C-2021 | OH | $NO_2$ | $(CH_2)_3NH(CH_2)_3$ | $CH_3$ |
| 11 | Ik | C-2022 | H | $CH_3$ | $(CH_2)_3NH(CH_2)_3$ | $CH_3$ |
| 12 | Il | C-2023 | H | $CH_3$ | $(CH_2)_3NCH_3(CH_2)_3$ | $CH_3$ |
| 13 | Im | C-2024 | H | $CH_3$ | $(CH_2)_2NH(CH_2)_2NH(CH_2)_2$ | $CH_3$ |
| 14 | In | C-2026 | H | $NO_2$ | $(CH_2)_3NCH_3(CH_2)_3$ | H |
| 15 | Io | C-2029 | H | $NO_2$ | $(CH_2)_3NCH_3(CH_2)_3$ | $CH_3$ |
| 16 | Ip | C-2030 | H | $NO_2$ | $(CH_2)_3$piperazinyl$(1,4)(CH_2)_3$ | $CH_3$ |
| 17 | Ir | C-2031 | H | $NO_2$ | $(CH_2)_3$piperazinyl$(1,4)(CH_2)_3$ | H |
| 18 | Is | C-2032 | H | $NO_2$ | $(CH_2)_2NH(CH_2)_2NH(CH_2)_2$ | $CH_3$ |
| 19 | It | C-2033 | H | $NO_2$ | $(CH_2)_2NH(CH_2)_2NH(CH_2)_2$ | H |
| 20 | Iu | C-2038 | H | $CH_3$ | $(CH_2)_3NH(CH_2)_3$ | H |
| 21 | Iw | C-2039 | H | $NO_2$ | $(CH_2)_3NH(CH_2)_2NH(CH_2)_3$ | $CH_3$ |
| 22 | Ix | C-2040 | H | $NO_2$ | $(CH_2)_3NH(CH_2)_2NH(CH_2)_3$ | H |

The second subgroup of example compounds according to the present invention is constituted by asymmetric dimers of imidazoacridono-1-nitroacridine (II a-k). These compounds, defined by the general formula II, were obtained using the method shown in schematic 2.

A substantial stage of the synthesis is the preparation of derivatives of imidazoacridone 5. These were synthesized starting with nitroderivatives of 2, through reduction and immediate cyclisation of the resulting unstable amino derivatives. This method of synthesis was described in W. M. Cholody, S. Martelli et al., J. Med. Chem., 33 49-52, 1990; W. M. Cholody, S. Martelli, J. Konopa, J. Med. Chem., 33 10, 2852-2856, 1990; M. T. Konieczny, J. K. Konopa, GB 2317888. The final stage of the synthesis was the condensation of the derivatives of 5 a-g with derivatives of 9-phenoxy-1-nitroacridine (3 a and b). The resulting final products were purified three times by way of column chromatography, in order to obtain compounds of the required purity to perform biological tests.

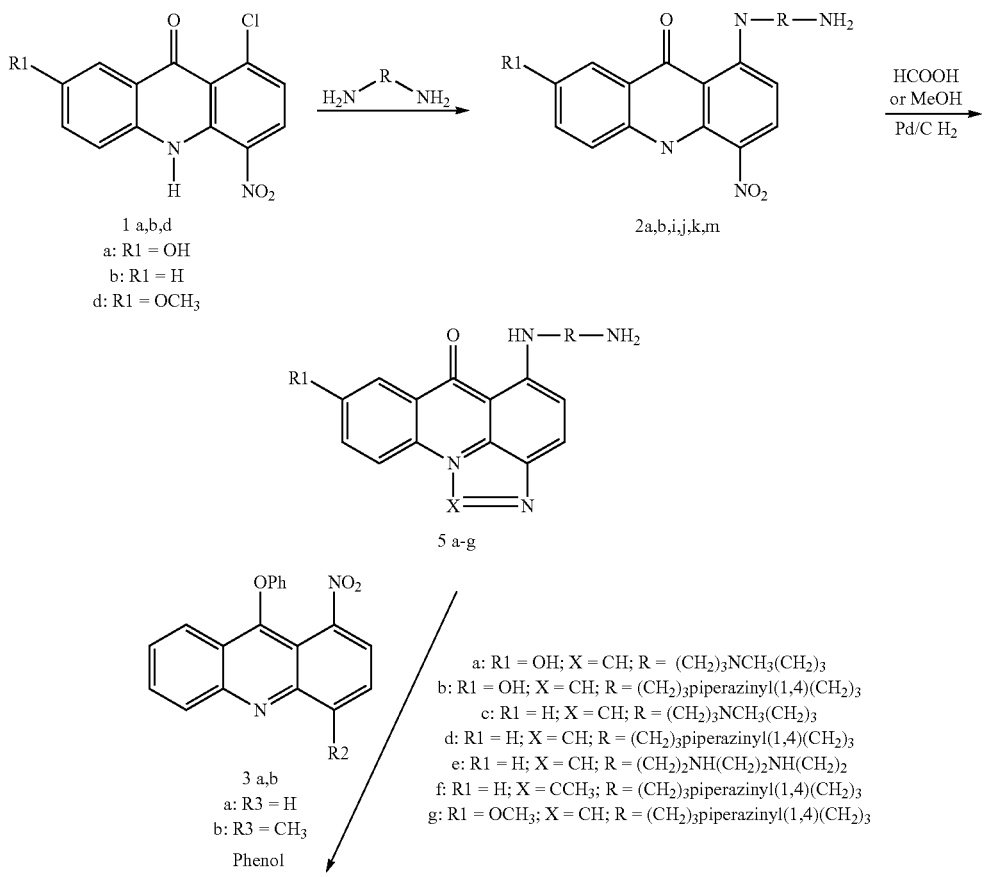

Schematic 2. Synthesis of asymmetric acridine dimers of imidazoacridono-1-nitroacridine (II a-k).

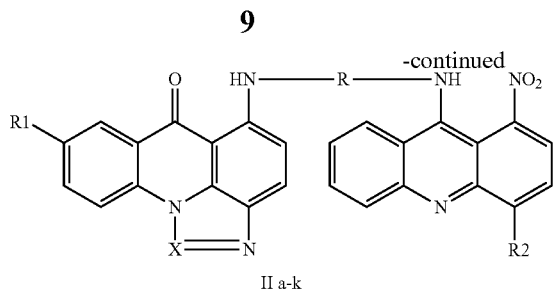

II a-k

TABLE 2

Asymmetric dimers of imidazoacridono-1-nitroacridine
(II a-k) obtained according to schematic 2.

| EXAMPLE | NO. | CODE | R1 | R | R2 |
|---|---|---|---|---|---|
| 23 | II a | C-2025 | OH | $(CH_2)_3$piperazinyl(1,4)$(CH_2)_3$ | $CH_3$ |
| 24 | II b | C-2027 | OH | $(CH_2)_3$piperazinyl(1,4)$(CH_2)_3$ | H |
| 25 | II c | C-2028 | H | $(CH_2)_3NCH_3(CH_2)_3$ | H |
| 26 | II d | C-2037 | H | $(CH_2)_2NH(CH_2)_2NH(CH_2)_2$ | H |
| 27 | II e | C-2041 | H | $(CH_2)_3$piperazinyl(1,4)$(CH_2)_3$ | H |
| 28 | II f | C-2042 | OH | $(CH_2)_3NCH_3(CH_2)_3$ | H |
| 29 | II g | C-2045 | OH | $(CH_2)_3NCH_3(CH_2)_3$ | $CH_3$ |
| 30 | II h | C-2049 | $OCH_3$ | $(CH_2)_3$piperazinyl(1,4)$(CH_2)_3$ | H |
| 31 | II i | C-2050 | H | $(CH_2)_3$piperazinyl(1,4)$(CH_2)_3$ | $CH_3$ |
| 32 | II j | C-2051 | OH | $(CH_2)_3$piperazinyl(1,4)$(CH_2)_3$ | H |
| 33 | II k | C-2053 | H | $(CH_2)_3NCH_3(CH_2)_3$ | $CH_3$ |

The third subgroup of example compounds according to the present invention is constituted by asymmetric dimers of triazoloacridono-1-nitroacridine (III a-j)

These compounds, shown by the general formula III, were obtained using the method described in schematic 3. The synthesis of substrates (7 a-e) used in the condensation of acridine derivatives, was performed using an analogous or similar method to the publication [Cholody et al.; *J. Med. Chem.*, 1990, 33, 10, 2852-2856]. The previously synthesized compounds (1a and 1b) were subjected to a reduction reaction, and then closing the triazole ring. The condensation of the derivatives of 1-chlorotriazoloacridone (6) was performed in DMSO or DMA with an excess of the appropriate aliphatic amine. The resulting derivatives of 7 were purified through crystallization. Derivatives of these were then condensed with the previously synthesized derivatives of 9-phenoxy-1-nitroacridine (3 a and b) in phenol. To obtain each of the products (III a-j), were designed condensation conditions (reaction time and temperature). The products were purified through crystallization and/or column chromatography.

Schematic 3. Synthesis of derivatives defined by the structural formula III a-j

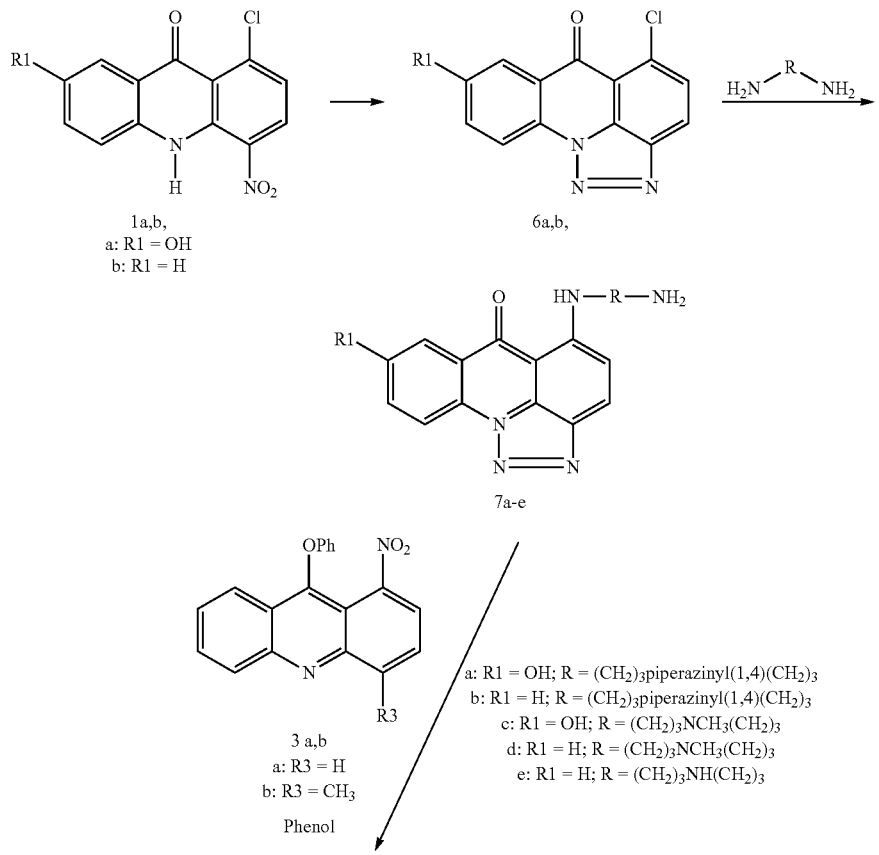

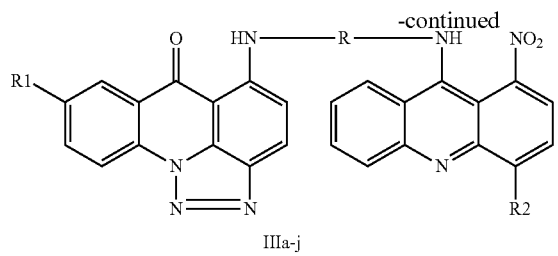

IIIa-j

TABLE 3

Asymmetric dimers of triazoloacridono-1-nitroacridine (III a-j) obtained according to schematic 3.

| EXAMPLE | NO. | CODE | R1 | R | R2 |
|---|---|---|---|---|---|
| 34 | III a | C-2047 | OH | $(CH_2)_3$piperazinyl(1,4)$(CH_2)_3$ | H |
| 35 | III b | C-2048 | H | $(CH_2)_3$piperazinyl(1,4)$(CH_2)_3$ | H |
| 36 | III c | C-2052 | OH | $(CH_2)_3NCH_3(CH_2)_3$ | H |
| 37 | III d | C-2056 | OH | $(CH_2)_3NCH_3(CH_2)_3$ | $CH_3$ |
| 38 | III e | C-2057 | OH | $(CH_2)_3$piperazinyl(1,4)$(CH_2)_3$ | $CH_3$ |
| 39 | III f | C-2058 | H | $(CH_2)_3$piperazinyl(1,4)$(CH_2)_3$ | $CH_3$ |
| 40 | III g | C-2060 | H | $(CH_2)_3NCH_3(CH_2)_3$ | H |
| 41 | III h | C-2061 | H | $(CH_2)_3NCH_3(CH_2)_3$ | $CH_3$ |
| 42 | III i | C-2062 | H | $(CH_2)_3NH(CH_2)_3$ | $CH_3$ |
| 43 | III j | C-2063 | H | $(CH_2)_3NH(CH_2)_3$ | H |

Example bis-acridines according to the present invention were obtained in the form of salts, such as hydrochloride or methanesulphonates, with a purity 99.7% or higher. Their structures were confirmed using spectral methods: proton magnetic resonance, elemental analysis, and the purity of these compounds was ascertained using thin-layer chromatography TLC as well as high-performance liquid chromatography. Salts in a solid state are stable for over a year over a desiccant. However, in aqueous solutions, these are much less stable. All of the synthesized derivatives are hydroscopic. All of bis-acridines hydrochlorides are characterized by good water solubility (studies were carried out for solutions of 1 mmol as well as 1 μmol). This is very preferable, because it is conditional for intravenous and intraperitoneal administration. Bis-acridines methanesulphonate solubility in water is even higher than of hydrochlorides.

Melting points were determined on a Stuart SMP30 capillary apparatus and are uncorrected. $^1$H NMR spectra were recorded on a Varian VXR-S spectrometer operating at 500 MHz. Chemical shifts are reported as δ units in ppm downfield from internal tetramethylsilane. NMR abbreviations used are as follows: br.s-broad signal, s-singlet, d-doublet, dd-doublet of doublets, t-triplet, k-quartet, m-multiple. The results of elemental analyses for individual elements fit within ±0.4% of theoretical values.

EXAMPLE 1

Preparation of dimer Ia (C-1906): 9-{N-[(7-hydroxy-4-nitro-9(10H)acridono-1-yl)aminopropyl]-N-methylaminopropylamino}-1'-nitroacridone×2HCl. A mixture of derivative 2a (0.002 mol), 15 ml phenol and 9-phenoxy-1-niroacridine (3a) (0.002 mol) was stirred at 90° C. for 24 h. After cooling, the reaction mixture was dissolved in methanol (~10 ml) and then poured into diethyl ether (~100 ml) and then stirred for 0.5 h. The precipitate was collected by filtration and washed with ether and acetone. The product was crystallized from acetone-water. Yield 51%, m.p. 228-229° C. Elemental analysis: $C_{33}H_{33}N_7O_6Cl_2×4H_2O$. $^1$H NMR (Me$_2$SO-d$_6$+TFA) δ: 14.00 (br.s, 1H, N10'-H$^+$); 12.41 (s, 1H, N10-H); 11.96 (m, 1H, N1HCH$_2$); 10.74 (br.s, 1H, CH$_2$NCH$_3$—H$^+$CH$_2$); 10.52 (br.s, 1H, N9'-H); 8.44-8.56 (m, 1H, C8'); 8.35 (d, J=9.8 Hz, 1H, C3); 8.12-8.24 (m, 2H, C5', C2'); 7.93-8.06 (m, 2H, C6', C3'); 7.84-7.89 (m, 2H, C4', C5); 7.55-7.62 (m, 1H, C7'); 7.50 (s, 1H, C8); 7.28 (dd, J$_1$=8.8 Hz, J$_2$=2.7 Hz, 1H, C6); 6.58 (d, J=9.8 Hz, 1H, C2); 3.60-3.69 (m, 2H, CH$_2$N9'-H); 3.50-3.58 (m, 2H, N1HCH$_2$); 2.96-3.19 (m, 4H, CH$_2$NCH$_3$CH$_2$); 2.70 (s, 3H, CH$_2$NCH$_3$CH$_2$); 2.02-2.10 (m, 2H, CH$_2$CH$_2$CH$_2$N9'-H); 2.10-2.19 (m, 2H, N1HCH$_2$CH$_2$CH$_2$)

Synthesis of derivative 2a: 1-{3-[N-(3-Aminopropyl)-N-methylamino]propylamino}-7-hydroxy-4-nitro-9(10H)-acridone×2HCl. A mixture of 1-chloro-7-hydroxy-4-nitro-9(10H)-acridone (1a) (1.45 g, 0.005 mol), and 3,3-diamino-N-methyldipropylamine 2.90 g (0.02 mol) in DMSO (25 ml) was stirred at room temperature for 2.5 h. After this time, water was added (~200 ml) and the reaction mixture was stirred for 0.5 h. The precipitate was collected by filtration. Next, it was transferred into water, acidified with a dilute hydrochloric acid and stirred for 0.5 h. Undissolved material was filtered off, and the solution was evaporated to a small volume. The product was precipitated out using acetone (~100 ml), and then was filtered off to give 1.2 g (51%).

EXAMPLE 2

Preparation of dimer Ib (C-1941):1-[3-(7-hydroxy-4-nitro-9(10H)-acridono-1-yl)aminopropyl]-4-3'-(1'-nitroacridin-1-yl)-aminopropyl]piperazine×3HCl. The method of preparation was similar to that in the case of derivative Ia: 2b and 3a were used in the synthesis; yield 63%, m.p. 223-224° C. Elemental analysis: $C_{36}H_{33}N_8O_6Cl_3×2H_2O$. $^1$H NMR (Me$_2$SO-d$_6$+TFA) δ: 12.38 (s, 1H, N10-H); 11.93 (m, 1H, N1HCH$_2$); 8.48-8.56 (m, 1H, C8'); 8.38 (d, J=9.8 Hz, 1H, C3); 8.17-8.22 (m, 1H, C2'); 8.04-8.12 (m, 1H, C4'); 7.94-8.00 (m, 1H, C3'); 7.88-7.94 (m, 2H, C5', C6'); 7.77 (d, 1H, C5); 7.58 (s, 1H, C8); 7.52-7.58 (m, 1H, C7'); 7.30 (dd, J$_1$=8.8 Hz, J$_2$=2.7 Hz, 1H, C6); 6.61 (d, J=9.8 Hz, 1H, C2); 3.67-3.75 (m, 2H, CH$_2$N9'-H); 3.57-3.64 (m, 2H, N1HCH$_2$); 3.22-3.57 (m, 8H, N(CH$_2$CH$_2$)$_2$N); 3.07-3.22 (m, 2H, N1HCH$_2$CH$_2$CH$_2$N); 2.93-3.07 (m, 2H, NCH$_2$CH$_2$CH$_2$N9'H); 2.10-2.21 (m, 4H, N1HCH$_2$CH$_2$CH$_2$; CH$_2$CH$_2$CH$_2$N9'-H). Preparation of derivative2b:1-(Aminopropyl)-4[N-(7-hydroxy-4-nitro-9(10H)-acridono-1-yl)-3-aminopropyl]piperazine×3HCl. The method of preparation was similar to that in the case of derivative 2a: 1,4-Bis-(3-amionopropyl)piperazine was used; yield 64%.

EXAMPLE 3

Preparation of dimer Ic (C-1965):9-{N-[(4-methyl-9(10H)-acridono-1-yl)aminoethyl]ethylamino}-1'-nitroacridine×3HCl. The method of synthesis was similar to that in the case of derivative Ia. 2c and 3a were used, the reaction temperature—100° C. and the time was 12 h. The difference was in product purification, based on dissolving compound in water, alkalizing using an aqueous solution of $Na_2CO_3$ and extracting the aqueous phase with chloroform. The extract was washed three times with water and dried using $MgSO_4$. The solvent was evaporated, and the crude product was purified by silica gel chromatography. The initial eluent was $CHCl_3$, and then $CHCl_3$/MeOH (20:1 v/v), (10:1 v/v), (5:1 v/v). The purified product in the form of a base, was dissolved in methanol (10 ml) and acidified with HCl/diethyl ether. Next, it was precipitated out with diethyl ether. Yield 53%, m.p. 252-254° C. Elemental analysis: $C_{31}H_{31}N_6O_3Cl_3 \times 3H_2O$. $^1H$ NMR ($Me_2SO$-$d_6$+TFA) δ: 10.80 (s, 1H, N10-H); 10.10 (s, 1H, N9'HCH$_2$); 9.98 (s, 1H, N1HCH$_2$); 8.13 (d, J=7.8 Hz, 1H, Ar—H); 7.91 (d, J=8.3 Hz, 1H, Ar—H); 7.82 (d, J=8.3 Hz, 1H, Ar—H); 7.64 (t, 1H, Ar—H); 7.50 (t, 2H, Ar—H); 7.35 (d, J=8.3 Hz, 1H, Ar—H); 7.24-7.31 (m, 3H, Ar—H); 7.19 (t, J=7.3 Hz, 1H, Ar—H); 7.06-7.12 (t, J=7.8 Hz, 1H, Ar—H); 6.19 (d, J=8.3 Hz, 1H, C2); 3.78-3.83 (m, 2H, CH$_2$N9'-H); 3.21-3.26 (m, 2H, N1HCH$_2$); 2.84-2.89 (m, 2H, CH$_2$NHCH$_2$); 2.75-2.80 (m, 2H, CH$_2$NHCH$_2$); 2.36 (s, 3H, Ar—CH$_3$). Preparation of derivative 2c: 1-{2-[N-(2-Aminoethylamino)ethyl] amino}-4-methyl-9(10H)-acridone×3HCl. A mixture of 1-chloro-4-methyl-9(10H)-acridone (1b) (1.5 g, 0.0062 mol) and diethyltriamine (10 ml) was stirred and heated at 150° C. for 24 h. After this time, the mixture was cooled to room temperature and then poured into water (100 ml) and then stirred for 0.5 h. The precipitate was collected by filtration, washed with water and dried. The product was purified by silica gel column chromatography using the initial eluent CHCl$_3$/MeOH at a ratio of (4:1 v/v) and then was CHCl$_3$/MeOH/NH$_3$ (3:1:0.01, v/v). The main fraction after evaporated was crystallized from chloroform-hexane. The crystals were dissolved in methanol (10 ml) and acidified with HO/diethyl ether. After adding of acetone (~100 ml) the desired product was obtained. Yield 53%.

EXAMPLE 4

Preparation of dimer Id (C-1973):1-[3-(4-methyl-9(10H)-acridono-1-yl)aminopropyl]-4-3'-[(1'-nitroacridin-1-yl)-aminopropyl]piperazine×4HCl. The method of synthesis and purification was similar to that in the case of derivative Ic: 2d and 3a were used; the reaction time was 26 h, yield 33%, m.p. 199-201° C. Elemental analysis: $C_{37}H_{43}N_7O_3Cl_4 \times 5H_2O$. $^1H$ NMR ($Me_2SO$-$d_6$+TFA) δ: 10.71 (s, 1H, N10-H); 10.12 (s, 1H, N9'HCH$_2$); 9.92-9.94 (m, 1H, N1HCH$_2$); 8.14 (d, J=7.8 Hz, 1H, Ar—H); 7.82 (d, J=8.3 Hz, 2H, Ar—H); 7.62-7.65 (t, 1H, Ar—H); 7.48 (t, J=7.8 Hz, 2H, Ar—H); 7.33-7.36 (m, 1H, C3); 7.24-7.29 (m, 3H, Ar—H); 7.17-7.20 (t, 1H, Ar—H); 7.07-7.10 (t, 1H, Ar—H); 6.19 (d, J=9.8 Hz, 1H, C2); 3.66-3.69 (m, 2H, CH$_2$N9'-H); 3.16-3.20 (m, 2H, N1HCH$_2$); 2.37-2.40 (m, 12H, CH$_2$N(CH$_2$CH$_2$)$_2$NCH$_2$); 2.36 (s, 3H, Ar—CH$_3$); 1.77-1.80 (m, 2H, CH$_2$CH$_2$CH$_2$N9'-H); 1.65-1.67 (m, 2H, N1HCH$_2$CH$_2$CH$_2$). Preparation of derivative 2d: 1-(Aminopropyl)-4-(N-(4-methyl-9(10H)acridono-1-yl)-3-aminopropyl]piperazine×4HCl. The method of synthesis was similar to that in the case of derivative 2c: 1,4-bis(3-N-aminopropyl)-piperazine was used; yield 68%.

EXAMPLE 5

Preparation of dimer Ie (C-1977):9-[N-(4-methyl-9(10H) acridono-1-yl)-aminoethylaminoethylamino-ethylamino]-1'-nitroacridine×4HCl. The method of synthesis and purification was similar to that in the case of derivative Ic: 2e and 3a were used; the reaction time was 30 h, yield 35%, m.p. 200-202° C. Elemental analysis: $C_{33}H_{37}N_7O_3Cl_4 \times 3H_2O$. $^1H$ NMR ($Me_2SO$-$d_6$+TFA) δ: 10.71 (s, 1H, N10-H); 10.12 (s, 1H, N9'HCH$_2$); 9.92-9.94 (m, 1H, N1HCH$_2$); 8.13 (d, J=7.8 Hz, 1H, Ar—H); 7.82 (d, J=8.3 Hz, 2H, Ar—H); 7.63 (t, J=7.8 Hz, 1H, Ar—H); 7.50 (k, J=7.8 Hz, 2H, Ar—H); 7.35 (d, J=8.3 Hz, 1H, C3); 7.27 (t, J=7.8 Hz, 3H, Ar—H); 7.16 (t, J=7.8 Hz, 1H, Ar—H); 7.05 (t, J=7.8 Hz, 1H, Ar—H); 6.18 (d, J=8.3 Hz, 1H, C2); 3.74-3.79 (m, 2H, CH$_2$N9'-H); 3.16-3.23 (m, 2H, N1HCH$_2$); 2.81-2.86 (m, 2H, NHCH$_2$CH$_2$N9'-H); 2.70-2.75 (m, 2H, N1HCH$_2$CH$_2$NH); 2.62-2.68 (m, 4H, NHCH$_2$CH$_2$NH); 2.36 (s, 3H, Ar—CH$_3$); 1.77-1.80 (m, 2H, CH$_2$CH$_2$CH$_2$N9'-H); 1.65-1.67 (m, 2H, N1HCH$_2$CH$_2$CH$_2$). Preparation of derivative 2e: 1-{2l-[2-(2Aminoethylamino)-ethylamino]-ethylamino}-4-methyl-9(10H)-acridone×4HCl. The method of synthesis was similar to that in the case of derivative 2c: triethylenetetraamine was used; yield 35%.

EXAMPLE 6

Preparation of dimer If (C-2016): 9-{N-[(4-methyl-9 (10H)-acridono-1-yl)aminoethyl]ethylamino}-4'-methyl-1'-nitroacridine×2CH$_3$SO$_2$OH. The method of synthesis and purification was similar to that in the case of derivative Ic: 2c and 3b were used, the reaction temperature—120° C., the time was 3 h. The purified product in the form of a base, was dissolved in methanol (10 ml) and acidified with methanesulphonic acid. After adding diethyl ether the desired product was obtained. Yield 39%, m.p. 106-108° C. Elemental analysis: $C_{34}H_{38}N_6O_9S_2 \times 3H_2O$. $^1H$ NMR ($Me_2SO$-$d_6$+TFA) δ: 10.77 (s, 1H, N10-H); 10.10 (s, 1H, N9'HCH$_2$); 9.96 (s, 1H, N1HCH$_2$); 8.14 (d, J=7.7 Hz, 1H, Ar—H); 7.88 (d, J=8.0 Hz, 1H, Ar—H); 7.82 (d, J=8.2 Hz, 1H, Ar—H); 7.67 (d, J=8.2 Hz, 1H, Ar—H); 7.64 (t, J=8.2 Hz, 1H, Ar—H); 7.51 (t, J=7.4 Hz, 1H, Ar—H); 7.37 (d, J=7.7 Hz, 1H, Ar—H); 7.27 (d, J=8.2 Hz, 1H, Ar—H); 7.22 (d, J=8.0 Hz, 1H, Ar—H); 7.19 (t, J=7.4 Hz, 1H, Ar—H); 7.12 (t, J=7.4 Hz, 1H, Ar—H); 6.19 (d, J=8.2 Hz, 1H, C2); 3.78-3.82 (m, 2H, CH$_2$N9'-H); 3.21-3.28 (m, 2H, N1HCH$_2$); 2.85-2.91 (m, 2H, CH$_2$NHCH$_2$); 2.77-2.82 (m, 2H, CH$_2$NHCH$_2$); 2.48 (s, 3H), 2.36 (s, 3H, Ar—CH$_3$).

EXAMPLE 7

Preparation of dimer Ig (C-2017):1-[3-(4-methyl-9(10H)-acridono-1-yl)aminopropyl]-1-[3'-(4'-methyl-1'-nitroacridin-1-yl)-aminopropyl]piperazine×3CH$_3$SO$_2$OH. The method of synthesis and purification was similar to that in the case of derivative If: 2d and 3b were used; yield 45%, m.p. 119-120° C. Elemental analysis: $C_{41}H_{53}N_6O_{12}S_3 \times 2H_2O$. $^1H$ NMR ($Me_2SO$-$d_6$+TFA) δ: 10.13 (s, 1H, N10-H); 9.94 (br.s, 1H, N9'HCH$_2$); 9.62 (s, 1H, N1HCH$_2$); 8.15 (d, J=8.3 Hz, 1H, Ar—H); 7.83 (d, J=8.3 Hz, 1H, Ar—H); 7.79 (d, J=7.8 Hz, 1H, Ar—H); 7.63-7.67 (m, 2H, Ar—H); 7.50 (t, J=7.8 Hz, 1H, Ar—H); 7.51 (t, J=7.4 Hz, 1H, Ar—H); 7.35-7.37 (m, 2H, Ar—H); 7.28 (d, J=7.8 Hz, 1H, Ar—H); 7.17-7.24 (m, 2H, Ar—H); 7.12 (t, J=7.8 Hz, 1H, Ar—H); 6.18 (d, J=8.3 Hz, 1H, C2); 3.62-3.69 (m, 2H, CH$_2$N9'-H); 3.15-3.22 (m, 2H, N1HCH$_2$); 2.47 (s, 3H, Ar—CH$_3$); 2.36-2.46 (m, 12H, CH$_2$N(CH$_2$CH$_2$)$_2$NCH$_2$); 2.36 (s, 3H, Ar—CH$_3$); 1.75-1.82 (m, 2H, CH$_2$CH$_2$CH$_2$N9'-H); 1.63-1.69 (m, 2H, N1HCH$_2$CH$_2$CH$_2$)

EXAMPLE 8

Preparation of dimer Ih (C-2019): 9-{N-[(7-hydroxy-4-nitro-9(10H)acridono-1-yl)aminopropyl]-N-methylaminopropylamino}-4'-methyl-1'-nitroacridine×2HCl. The method of synthesis and purification was similar to that in the case of derivative Ia: 2a and 3b were used; the reaction temperature—130° C., the time was 3 h, yield 34%, m.p. 215-217° C. Elemental analysis: $C_{34}H_{35}N_7O_6Cl_2 \times 3H_2O$. $^1$H NMR (Me$_2$SO-d$_6$+TFA) δ: 12.40 (s, 1H, N10-H); 11.97 (br.s, 1H, N1HCH$_2$); 10.04 (br.s, 1H, N9'-H); 8.36-8.42 (m, 1H, C8'), 8.35 (d, J=9.8 Hz, 1H, C3); 8.11-8.24 (m, 2H, C2', C5'); 7.97 (t, J=7.6 Hz, 1H, C3'); 7.81-7.91 (m, 2H, C5, C6'); 7.55-7.63 (m, 1H, C7'); 7.49 (s, 1H, C8); 7.27 (dd, J$_1$=8.8 Hz, J$_2$=2.4 Hz, 1H, C6); 6.56 (d, J=9.8 Hz, 1H, C2); 3.48-3.59 (m, 4H, CH$_2$N1,9'-H); 2.94-3.22 (m, 4H, CH$_2$NCH$_3$CH$_2$); 2.75 (s, 3H, Ar—CH$_3$); 2.73 (br.s, 3H, NCH$_3$); 2.10-2.19 (m, 4H, N1,9'HCH$_2$CH$_2$CH$_2$).

EXAMPLE 9

Preparation of dimer Ii (C-2020): 1-[3-(7-hydroxy-4-nitro-9(10H)-acridono-1-yl)aminopropyl]-4-[3'-(4'-methyl-1'-nitro-acridin-1-yl)-aminopropyl]piperazine×3HCl. The method of synthesis and purification was similar to that in the case of derivative Ia: 2b and 3b were used; the reaction temperature—140° C., the time was 3 h, yield 39%, m.p. 225-227° C. Elemental analysis: $C_{37}H_{41}N_8O_6Cl_3 \times 4H_2O$. $^1$H NMR (Me$_2$SO-d$_6$+TFA) δ: 12.44 (s, 1H, N10-H); 11.99 (br.s, 1H, N1HCH$_2$); 8.40-8.42 (m, 1H, C8'), 8.38 (d, J=9.8 Hz, 1H, C3); 8.16-8.22 (m, 2H, C2', C5'); 7.97 (t, J=7.6 Hz, 1H, C6'); 7.81-7.93 (m, 2H, C5, C3'); 7.57-7.68 (m, 1H, C7'); 7.53 (s, 1H, C8); 7.28 (dd, J$_1$=8.8 Hz, J$_2$=2.4 Hz, 1H, C6); 6.59 (d, J=9.8 Hz, 1H, C2); 3.07-3.80 (m, 16H, Alif-H); 2.01-2.17 (m, 4H, N1,9'HCH$_2$CH$_2$CH$_2$)

EXAMPLE 10

Preparation of dimer Ij (C-2021): 9-{N-[(7-hydroxy-4-nitro-9(10H)acridono-1-yl)aminopropyl]-aminopropylamino}-4'-methyl-1'-nitroacridine×2HCl. The method of synthesis and purification was similar to that in the case of derivative Ia: 2f and 3b were used; the reaction temperature—140° C., the time was 4 h, yield 37%, m.p. 221-223° C. Elemental analysis: $C_{33}H_{33}N_7O_6Cl_2 \times 4H_2O$. $^1$H NMR (Me$_2$SO-d$_6$+TFA) δ: 12.43 (s, 1H, N10-H); 11.95 (br.s, 1H, N1HCH$_2$); 8.37 (d, J=9.8 Hz, 1H, C3,); 8.35-8.37 (m, 1H, C8'); 8.12-8.22 (m, 2H, C3', C5'); 7.92-8.03 (m, J=7.6 Hz, 1H, C6'); 7.78-7.92 (m, 2H, C5, C2'); 7.56-7.63 (m, 1H, C7'); 7.51 (s, 1H, C8); 7.26 (dd, J$_1$=8.8 Hz, J$_2$=2.4 Hz, 1H, C6); 6.56 (d, J=9.8 Hz, 1H, C2); 3.46-3.64 (m, 4H, CH$_2$N1,9'-H); 2.88-3.09 (m, 4H, CH$_2$NHCH$_2$); 2.74 (s, 3H, Ar—CH$_3$); 1.99-2.15 (m, 4H, N1,9'HCH$_2$CH$_2$CH$_2$). —Preparation of derivative 2f: 1-{3-[N-(3-Aminopropyl)]propylamino}-7-hydroxy-4-nitro-9(10H)-acridone×2HCl. The method of synthesis was similar to that in the case of derivative 2a: bis(3-aminopropyl)amine was used; yield 56%.

EXAMPLE 11

Preparation of dimer Ik (C-2022):9-{N-[(4-methyl-9 (10H)-acridono-1-yl)aminopropyl]propylamino}-4'-methyl-1'-nitroacridine×3HCl. The method of synthesis was similar to that in the case of derivative Ia. 2g and 3b were used, the reaction temperature—100° C., the time was 2.5 h. The difference was in product purification, based on dissolving compounds in water, alkalizing using an aqueous solution of Na$_2$CO$_3$ and extracting the aqueous phase with chloroform. The extract was washed three times with water and dried using MgSO$_4$. The solvent was evaporated, and crude product was purified by silica gel column chromatography. The initial eluent was CHCl$_3$/MeOH (5:1 v/v) and then was CHCl$_3$/MeOH/NEt$_3$ (5:1:0.1 v/v). The purified product in the form of a base, was dissolved in methanol (10 ml) and acidified HCl/diethyl ether. After adding diethyl ether the desired product was obtained. Yield 43%, m.p. 207-209° C. Elemental analysis: $C_{34}H_{37}N_6O_3Cl_3 \times 2H_2O$. $^1$H NMR (Me$_2$SO-d$_6$) δ: 12.31 (s, 1H, N10'-H); 11.02 (s, 1H, N10-H); 10.21 (br.s, 1H, N9'HCH$_2$); 9.15 (s, 1H, N1HCH$_2$); 8.30-8.32 (m, 1H, Ar—H); 8.16-8.17 (m, 1H, Ar—H); 8.11 (d, J=7.3 Hz, 1H, Ar—H); 7.98-7.99 (m, 1H, Ar—H); 7.84-7.90 (m, 2H, Ar—H); 7.58-7.65 (m, 2H, Ar—H); 7.28 (d, J=8.3 Hz, 1H, C3); 7.18 (t, J=7.3 Hz, 1H, Ar—H); 6.20 (d, J=8.3 Hz, 1H, C2); 3.59-3.82 (m, 2H, CH$_2$N9'-H); 3.24-3.27 (m, 2H, N1HCH$_2$); 2.88-2.98 (m, 4H, CH$_2$NHCH$_2$); 2.78 (s, 3H, Ar—CH$_3$); 2.36 (s, 3H, Ar—CH$_3$); 2.09-2.16 (m, 2H, CH$_2$CH$_2$CH$_2$N9'-H); 1.95-2.02 (m, 2H, N1HCH$_2$CH$_2$CH$_2$). Preparation of derivative 2g: 1-{3-[N-(3-Aminopropyl)]propylamino}-4-methyl-9(10H)-acridone×3HCl. The method of synthesis was similar to that in the case of derivative 2c: bis(3-aminopropyl)amine was used; yield 33%.

EXAMPLE 12

Preparation of dimer Il (C-2023): 9-{N-[(4-methyl-9 (10H)-acridono-1-yl)aminopropyl]-N-methylaminopropylamino}-4'-methyl-1'-nitroacridine×3HCl. The method of synthesis and purification was similar to that in the case of derivative Ik. 2h and 3b were used, the reaction temperature—100° C., the time was 1.5 h, yield 52%, m.p. 135-137° C. Elemental analysis: $C_{35}H_{39}N_6O_3Cl_3 \times 2H_2O$. $^1$H NMR (Me$_2$SO-d$_6$, base) δ: 10.18 (s, 1H, N10-H); 9.98 (br.s, 1H, N9'HCH$_2$); 9.75 (s, 1H, N1HCH$_2$); 8.13 (d, J=7.3 Hz, 1H, Ar—H); 7.84 (d, J=8.3 Hz, 1H, Ar—H); 7.74-7.81 (d, 1H, Ar—H); 7.69 (d, J=8.3, 1H, Ar—H); 7.65 (t, J=7.6 Hz, 1H, Ar—H); 7.52 (t, J=7.6 Hz, 1H, Ar—H); 7.36 (d, J=7.8 Hz, 1H, Ar—H); 7.28 (d, J=8.3 Hz, 1H, Ar—H); 7.17-7.24 (m, 2H, Ar—H); 7.12 (t, J=7.6 Hz, 1H, Ar—H); 6.21 (d, J=7.8 Hz, 1H, C2); 3.72 (m, 2H, CH$_2$N9'-H); 3.23-3.29 (m, 2H, N1HCH$_2$); 3.14-3.22 (m, 4H, CH$_2$NCH$_3$CH$_2$); 2.78 (s, 3H, Ar—CH$_3$); 2.36 (s, 3H, Ar—CH$_3$); 1.98-2.09 (m, 2H, CH$_2$CH$_2$CH$_2$N9'-H); 1.84-1.94 (m, 2H, N1HCH$_2$CH$_2$CH$_2$). Preparation of derivative 2h: 1-{3-[N-(3-Aminopropyl)-N-methylamino]propylamino}-4-methyl-9(10H)-acridone× 3HCl. A mixture of 1-chloro-4-methyl-9(10H)-acridone (1b) (2.0 g, 0.0082 mol) and 3,3-diamino-N-methyldipropylamine (10 ml) were reacted using a microwave reactor. The synthesis parameters were: the efficiency of the microwave reactor was P=25%, t$_{min}$=120° C., t$_{max}$=130° C., the conduct time was 1 h. After this time, the mixture was cooled to room temperature and then poured into water (100 ml) and extracted with chloroform. The product was purified by column chromatography. The initial eluent was CHCl$_3$/MeOH (4:1 v/v) and then CHCl$_3$/MeOH/NH$_3$ (3:1:0.01, v/v). Fractions containing the desired product were evaporated, and then it was dissolved in methanol (10 ml) and acidified with HO/diethyl ether. After adding acetone the desired product was obtained. Yield 47%.

EXAMPLE 13

Preparation of dimer Im (C-2024):9-[N-(4-methyl-9 (10H)acridono-1-yl)-aminoethylaminoethylamino-ethylamino]-4'-methyl-1'-nitroacridine×4HCl. The method of synthesis and purification was similar to that in the case of derivative 1k. 2e and 3b were used, the reaction temperature—100° C., the time was 3 h, yield 33%, m.p. 219-220°

C. Elemental analysis: $C_{34}H_{39}N_7O_3Cl_4 \times 4H_2O$. $^1H$ NMR ($Me_2SO$-$d_6$+TFA) δ: 10.20 (s, 1H, N10-H); 10.07 (br.s, 1H, N9'HCH$_2$); 9.15 (s, 1H, N1HCH$_2$); 8.30 (d, J=8.3 Hz, 1H, Ar—H); 8.18 (d, J=7.8 Hz, 1H, Ar—H); 8.12 (d, J=8.3 Hz, 1H, Ar—H); 7.96 (t, J=7.8 Hz, 1H, Ar—H); 7.88 (d, J=7.8 Hz, 1H, Ar—H); 7.83 (d, J=8.3 Hz, 1H, Ar—H); 7.59-7.64 (m, 2H, Ar—H); 7.26 (d, J=8.3 Hz, 1H, Ar—H); 7.17 (t, J=7.3 Hz, 1H, Ar—H); 6.25 (d, J=8.3 Hz, 1H, C2); 3.87-3.96 (m, 2H, CH$_2$N9'-H); 3.50-3.56 (m, 2H, N1HCH$_2$); 3.33-3.39 (m, 2H, NHCH$_2$CH$_2$NH); 3.14-3.22 (m, 6H, CH$_2$NHCH$_2$CH$_2$NH); 2.74 (s, 3H, Ar—CH$_3$); 2.34 (s, 3H, Ar—CH$_3$). Preparation of derivative 2e: 1-{2-[2-(2Aminoethylamino)-ethylamino]-ethylamino}-4-methyl-9(10H)-acridone×4HCl. The method of synthesis and purification was similar to that in the case of derivative 2h, triethyltetraamine was used. The reaction parameters in the microwave reactor were: P=30%, $t_{min}$=120° C., $t_{max}$=130° C., the process time was 45 min. Yield 40%.

EXAMPLE 14

Preparation of dimer In (C-2026): 9-{N-[(4-nitro-9(10H)acridono-1-yl)aminopropyl]-N-methylaminopropylamino}-1'-nitroacridine×2HCl. A mixture of 2i (0.0011 mol), 5 ml phenol and 9-phenoxy-1-niroacridine (3a) (0.0011 mol) was stirred at 90° C. for 6 h. After cooling, the reaction mixture was dissolved in methanol (~10 ml), poured into diethyl ether (~100 ml) and then stirred for 0.5 h. The precipitate was collected by filtration, washed with ether and then with acetone. The product was dissolved in methanol and small quantity of silica gel was added and solvent was evaporated. The remainder was loaded onto a dry chromatography column. The initial eluent was CHCl$_3$ and then CHCl$_3$/MeOH at a ratio of (15:1, 10:1 v/v), CHCl$_3$/MeOH/NH$_3$ (10:1:0.1 v/v). Yield 48%, m.p. 148-149° C. Elemental analysis: $C_{33}H_{33}N_7O_5Cl_2 \times 4H_2O$. $^1H$ NMR ($Me_2SO$-$d_6$+TFA) δ: 11.79 (br.s, 1H, N1HCH$_2$); 10.43 (br.s, 1H, CH$_2$NCH$_3$—H$^+$CH$_2$); 8.30 (d, J=9.8 Hz, 1H, C3); 8.20 (d, 1H, J=8.3 Hz, C8); 7.86 (d, J=8.3 Hz, 1H, C5); 7.71-7.79 (m, 2H, C6, C8'); 7.34-7.46 (m, 3H, C3', C6', C7); 7.29 (d, J=8.3 Hz, 1H, C4'); 7.24 (d, J=7.8 Hz, C5'); 7.15 (d, J=7.8 Hz, 1H, C2'); 7.00 (t, J=7.3 Hz, 1H, C7'); 6.52 (d, J=9.8 Hz, 1H, C2); 3.72 (t, J=5.9 Hz, 2H, CH$_2$N9'-H); 3.41-3.50 (m, 2H, CH$_2$N1-H); 2.42-3.50 (m, 4H, CH$_2$NCH$_3$CH$_2$); 2.20 (s, 3H, NCH$_3$); 1.80-1.83 (m, 2H, N1HCH$_2$CH$_2$CH$_2$); 1.70-1.72 (m, 2H, CH$_2$CH$_2$CH$_2$ N9'H). Preparation of derivative 2i: 1-{3-[N-(3-Aminopropyl)-N-methylamino]propylamino}-4-nitro-9(10H)-acridone×2HCl. A mixture of 1-chloro-4-nitro-9(10H)-acridone (1c) (0.01 mol), 3,3-diamino-N-methyldipropylamine (0.04 mol) in DMSO (50 ml) was stirred at room temperature for 3 h. After this time, water was added (~200 ml) and then stirred for 10 min. The precipitate was collected by filtration and suspended into water (~100 ml) and then acidified with a dilute hydrochloric acid and stirred again for 15 min. The insoluble precipitate was filtered off, and the filtrate was evaporated to a smaller volume. The product was precipitated out using acetone (~100 ml), and then was filtered off. Yield 81%.

EXAMPLE 15

Preparation of dimer Io (C-2029):9-{N-[(4-nitro-9(10H)acridono-1-yl)aminopropyl]-N-methylaminopropylamino}-4'-methyl-1'-nitroacridine×2HCl. The method of synthesis and purification was similar to that in the case of derivative In; 2i and 3b were used, the reaction temperature—120° C., the time was 12 h. Yield 57%, m.p. 187-189° C. Elemental analysis: $C_{34}H_{35}N_7O_5Cl_2 \times 4H_2O$. $^1H$ NMR ($Me_2SO$-$d_6$+TFA) δ: 12.37 (s, 1H, N10H); 11.80 (br.s, 1H, N1HCH$_2$); 10.39 (br.s, 1H, CH$_2$NCH$_3$—H$^+$CH$_2$); 8.38-8.50 (m, 1H, C3); 8.34 (d, 1H, J=9.8 Hz, C8); 8.21 (d, J=8.8 Hz, 1H, C2'); 8.14 (d, J=7.8 Hz, 2H, C5', C8'); 7.93-7.97 (m, 1H, C6'); 7.91 (d, J=8.8 Hz, 1H, C3'); 7.86 (t, J=7.8 Hz, 1H, C5); 7.74 (t, J=7.6 Hz, 1H, C7); 7.54-7.62 (m, 1H, C7'); 7.36 (d, J=7.6 Hz, C6); 6.59 (d, J=9.8 Hz, 1H, C2); 3.48-3.70 (m, 4H, CH$_2$N1,9'-H); 3.06-3.20 (m, 4H, CH$_2$NCH$_3$CH$_2$); 2.74 (s, 3H, A-CH$_3$); 2.71 (br.s, 3H, NCH$_3$); 2.00-2.20 (m, 4H, N1HCH$_2$CH$_2$CH$_2$, CH$_2$CH$_2$CH$_2$ N9'H).

EXAMPLE 16

Preparation of dimer Ip (C-2030):1-[3-(4-nitro-9(10H)-acridono-1-yl)aminopropyl]-4-[3'-(4'-methyl-1'-nitroacridin-1-yl)-aminopropyl]piperazine×3HCl. The method of synthesis and purification was similar to that in the case of derivative In; 2j and 3b were used. The reaction temperature—140° C., the time was 3.5 h. Yield 46%, m.p. 211-213° C. Elemental analysis: $C_{37}H_{41}N_8O_5Cl_3 \times 2H_2O$. $^1H$ NMR ($Me_2SO$-$d_6$+TFA) δ: 12.44 (s, 1H, N10H); 11.87 (br.s, 1H, N1HCH$_2$); 8.42 (d, J=9.8 Hz, 1H, C3); 8.34-8.40 (m, 1H, C8); 8.15-8.24 (m, 3H, C2', C5', C8'); 7.94-8.02 (m, 2H, C6', C3'); 7.90 (d, J=7.3 Hz, 1H, C5); 7.78 (t, J=7.3, 1H, C7); 7.58-7.65 (t, 1H, C7'); 7.40 (t, J=7.6 Hz, 1H, C6); 6.64 (d, J=9.8 Hz, 1H, C2); 3.53-3.62 (m, 4H, CH$_2$N9'-H, CH$_2$N1-H); 3.29-3.33 (m, 4H, CH$_2$N(CH$_2$CH$_2$)$_2$NCH$_2$); 3.06-3.15 (m, 8H, CH$_2$N(CH$_2$CH$_2$)$_2$NCH$_2$); 2.75 (s, 3H, Ar—CH$_3$); 2.00-2.13 (m, 4H, N1HCH$_2$CH$_2$CH$_2$, CH$_2$CH$_2$CH$_2$ N9'H). Preparation of derivative 2j: 1-(Aminopropyl)-4 [N-(4-nitro-9(10H)-acridono-1-yl)-3-aminopropyl]piperazine×3HCl. The method of synthesis was similar to that in the case of derivative 2i: 1,4-bis(3-N-aminopropyl)-piperazine was used; yield 73%.

EXAMPLE 17

Preparation of dimer Ir (C-2031):1-[3-(4-nitro-9(10H)-acridono-1-yl)aminopropyl]-4-[3'-(1'-nitroacridin-1-yl)-aminopropyl]piperazine×3HCl. The method of synthesis and purification was similar to that in the case of derivative In, 2j and 3a were used. The reaction temperature—90° C., the time was 12 h, yield 55%, m.p. 204-206° C. Elemental analysis: $C_{36}H_{39}N_8O_5Cl_3 \times 3H_2O$. $^1H$ NMR ($Me_2SO$-$d_6$+TFA) δ: 12.43 (s, 1H, N10H); 11.85 (br.s, 1H, N1HCH$_2$); 10.72 (s, 1H, N9'HCH$_2$); 8.35 (d, J=9.8 Hz, 2H, C3); 8.19 (d, 1H, J=7.8 Hz, C8); 7.93 (d, J=8.3 Hz, 1H, C5'); 7.81 (d, J=7.8 Hz, 1H, C8'); 7.75 (t, J=7.3 Hz, 1H, C6'); 7.44-7.52 (m, 2H, C3', C7); 7.38 (t, J=7.3 Hz, C7'); 7.33 (d, J=8.3 Hz, 1H, C5); 7.23-7.30 (m, 2H, C2', C4'); 7.08 (t, J=7.6 Hz, C6); 6.60 (d, J=9.8 Hz, 1H, C2); 3.62-3.69 (m, 2H, CH$_2$N9'-H); 3.43-3.53 (m, 2H, CH$_2$N1-H); 2.95-3.35 (m, 12H, CH$_2$N(CH$_2$CH$_2$)$_2$NCH$_2$); 1.80-1.83 (m, 2H, N1HCH$_2$CH$_2$CH$_2$); 1.70-1.72 (m, 2H, CH$_2$CH$_2$CH$_2$ N9'H)

EXAMPLE 18

Preparation of dimer Is (C-2032):9-[N-(4-nitro-9(10H)acridono-1-yl)-aminoethylaminoethylamino-ethylamino]-4'-methyl-1'-nitroacridine×3HCl. The method of synthesis and purification was similar to that in the case of derivative Ip; 2k and 3b were used, the reaction temperature—100° C., the time was 3 h, yield 34%, m.p. 206-208° C. Elemental analysis: $C_{33}H_{35}N_8O_5Cl_3 \times 4H_2O$. $^1H$ NMR ($Me_2SO$-$d_6$+TFA) δ: 12.38 (s, 1H, N10H); 11.81 (br.s, 1H, N1HCH$_2$); 9.23 (br.s, 2H, NH alif.); 8.44-8.54 (m, 1H, C3); 8.40 (d, 1H, J=9.8 Hz, C8); 8.16-8.24 (m, 3H, C2', C5', C8'); 7.94-8.02 (m, 2H, C6', C3'); 7.89 (d, J=7.8 Hz, 1H, C5); 7.74-7.80 (t, 1H, C7); 7.59-7.66 (t, 1H, C7'); 7.39 (t, J=7.6 Hz, 1H, C6); 6.68 (d, J=9.8 Hz, 1H, C2); 3.85-3.98 (m, 2H, C$\underline{H}_2$N9'-H); 3.77-3.85 (m, 2H, C$\underline{H}_2$N1-H); 3.31-3.43 (m, 4H, N1HCH$_2$C $\underline{H}_2$' C$\underline{H}_2$CH$_2$N9'H); 3.13-3.28 (m, 4H, NHC$\underline{H}_2$C$\underline{H}_2$NH); 2.76 (s, 3H, Ar—CH$_3$). Preparation of derivative 2k: 1-{2-[2-(2-Aminoethylamino)-ethylamino]-ethylamino}-4-nitro-9(10H)-acridone×3HCl. The method of synthesis was similar to that in the case of derivative 2i: triethylenetetraamine was used; yield 51%.

EXAMPLE 19

Preparation of dimer It (C-2033):9-[N-(4-nitro-9(10H) acridono-1-yl)-aminoethylaminoethylamino-ethylamino]-1'-nitroacridine×3HCl. The method of synthesis and purification was similar to that in the case of derivative In; 2k and 3a were used, the reaction temperature—90° C., the time was 12 h, yield 48%, m.p. 241-242° C. Elemental analysis: C$_{32}$H$_{33}$N$_8$O$_5$Cl$_3$×2H$_2$O. $^1$H NMR (Me$_2$SO-d$_6$+TFA) δ: 12.47 (s, 1H, N10$\underline{H}$); 11.71 (br.s, 1H, N1$\underline{H}$CH$_2$); 10.59 (s, 1H, N10'HCH$_2$); 8.37 (d, J=9.8 Hz, 2H, C3); 7.91 (d, J=7.8 Hz, 1H, C5'); 7.87 (d, J=8.3 Hz, 1H, C8); 7.59-7.70 (m, 2H, Ar—H); 7.32-7.39 (m, 1H, Ar—H); 7.18-7.25 (m, 2H, Ar—H); 7.14 (t, J=7.6 Hz, 1H, Ar—H); 7.09 (d, J=8.3 Hz, 1H, Ar—H); 6.90 (d, J=8.3 Hz, 1H, Ar—H); 6.82 (t, J=7.6 Hz, 1H, Ar—H); 6.41 (d, J=9.8 Hz, 1H, C2); 3.99 (t, J=5.4 Hz, 2H, C$\underline{H}_2$N9'-H); 3.70-3.79 (m, 2H, C$\underline{H}_2$N1-H); 3.21-3.30 (m, 4H, N1HCH$_2$C$\underline{H}_2$' C$\underline{H}_2$CH$_2$N9'H); 3.09 (t, J=5.4 Hz, 2H, NHC$\underline{H}_2$CH$_2$NH); 2.90 (t, J=5.1 Hz, 2H, NHCH$_2$C $\underline{H}_2$NH).

EXAMPLE 20

Preparation of dimer Iu (C-2038):9-{N-[(4-methyl-9 (10H)-acridono-1-yl)aminopropyl]propylamino}-1'-nitroacridine×3HCl. The method of synthesis and purification was similar to that in the case of derivative In; 2g and 3a were used, the reaction temperature—90° C., the time was 5 h, yield 38%, m.p. 203-205° C. Elemental analysis: C$_{33}$H$_{35}$N$_6$O$_3$Cl$_3$×3H$_2$O. $^1$H NMR (Me$_2$SO-d$_6$+TFA) δ: 10.25 (s, 1H, N10-H); 8.82 (br.s, 1H, CH$_2$N$\underline{H}$CH$_2$); 8.47 (br.s, 1H, Ar—H); 8.22 (d, J=7.8 Hz, 1H, Ar—H); 7.13 (t, J=7.8 Hz, 2H, Ar—H); 7.99-8.05 (m, 2H, Ar—H); 7.81-7.90 (m, 2H, Ar—H); 7.61 (dt, J$_1$=19.3 Hz, J$_2$=7.7 Hz, 2H, Ar—H); 7.30 (d, J=8.3 Hz, 1H, C3); 7.18 (t, J=7.6 Hz, 1H, Ar—H); 6.26 (d, J=8.3 Hz, 1H, C2); 3.68 (br.s, 2H, C $\underline{H}_2$N9'-H); 3.27 (t, J=6.6 Hz, 2H, N1HC$\underline{H}_2$); 2.86-3.02 (m, 4H, C$\underline{H}_2$NHC$\underline{H}_2$); 2.35 (s, 3H, Ar—CH$_3$); 2.02-2.14 (m, 2H, CH$_2$C$\underline{H}_2$CH$_2$N9'-H); 1.91-2.02 (m, 2H, N1HCH$_2$C$\underline{H}_2$CH$_2$). Preparation of derivative 2g: 1-{3-[N-(3-Aminopropyl)]propylamino}-4-methyl-9(10H)-acridone×3HCl. The method of synthesis and purification was similar to that in the case of derivative 2h, diethyltriamine was used. The reaction parameters in the microwave reactor were: P=25%, t$_{min}$=120° C., t$_{max}$=130° C., the process time was 30 min. Yield 54%.

EXAMPLE 21

Preparation of dimer Iw (C-2039): 9-[N-(4-nitro-9(10H) acridono-1-yl)-aminopropylaminoethylamino-propylamino]-4'-methyl-1'-nitroacridine×3HCl. The method of synthesis and purification was similar to that in the case of derivative In; 2l and 3b were used. The reaction temperature—120° C., the time was 8 h. Yield 38%, m.p. 199-201° C. Elemental analysis: C$_{35}$H$_{39}$N$_8$O$_5$Cl$_3$×3H$_2$O. $^1$H NMR (Me$_2$SO-d$_6$+TFA) δ: 12.43 (s, 1H, N10H); 11.84 (br.s, 1H, N1$\underline{H}$CH$_2$); 8.44-8.54 (m, 1H, C3); 8.39 (d, 1H, J=9.8 Hz, C8); 8.13-8.24 (m, 3H, C2', C5', C8'); 7.97 (m, 2H, C6', C3'); 7.87 (d, J=7.3 Hz, 1H, C5); 7.78 (t, J=7.8 Hz, 1H, C7); 7.55-7.65 (t, 1H, C7'); 7.40 (t, J=7.3 Hz, 1H, C6); 6.65 (d, J=9.8 Hz, 1H, C2); 3.57-3.65 (m, 2H, CH$_2$N9'-H); 3.25-3.33 (m, 2H, C$\underline{H}_2$N1-H); 3.17-3.24 (m, 4H, N1HCH$_2$CH$_2$C$\underline{H}_2$, C $\underline{H}_2$CH$_2$CH$_2$N9'H); 3.04-3.13 (m, 2H, NHCH$_2$C$\underline{H}_2$NH); 2.90-3.03 (m, 2H, NHC$\underline{H}_2$CH$_2$NH); 2.75 (s, 3H, Ar—CH$_3$); 1.99-2.16 (m, 4H, N1HCH$_2$C$\underline{H}_2$CH$_2$, CH$_2$C$\underline{H}_2$CH$_2$ N9'H). Preparation of derivative 2l: 1-{3-[2-(3-Aminopropylamino)-ethylamino]-propylamino}-4-nitro-9(10H)-acridone×3HCl. The method of synthesis was similar to that in the case of derivative 2i: 1,2-Bis(3-aminopropylamino)ethane was used; yield 55%.

EXAMPLE 22

Preparation of dimer Ix (C-2040): 9-[N-(4-nitro-9(10H) acridono-1-yl)-aminopropylaminoethylamino-propylamino]-1'-nitroacridine×3HCl. The method of synthesis and purification was similar to that in the case of derivative In; 2l and 3b were used, the reaction temperature—90° C., the time was 4 h. Yield 39%, m.p. 211-213° C. Elemental analysis: C$_{34}$H$_{37}$N$_8$O$_5$Cl$_3$×4H$_2$O. $^1$H NMR (Me$_2$SO-d$_6$+ TFA) δ: 12.43 (s, 1H, N10$\underline{H}$); 11.77 (br.s, 1H, N1$\underline{H}$CH$_2$); 10.74 (br.s, 1H, N9'HCH$_2$); 9.49-9.55 (br.s, 2H, NH alif.); 8.51 (br.s, 1H, Ar—H); 8.30 (d, J=9.8 Hz, 1H, Ar—H); 8.19 (d, J=7.3 Hz, 1H, Ar—H); 8.08-8.17 (m, 2H, Ar—H); 7.99 (t, J=8.1 Hz, 1H, Ar—H); 7.92-7.97 (m, 1H, Ar—H); 7.83-7.87 (m, 2H, Ar—H); 7.69-7.75 (m, 1H, Ar—H); 7.58 (t, J=7.6 Hz, 1H, Ar—H); 7.32-7.37 (m, 1H, Ar—H); 6.57 (d, J=9.8 Hz, 1H, C2); 3.62-3.77 (m, 2H, C$\underline{H}_2$N9'-H); 3.52-3.62 (m, 2H, m, 2H, N1HC$\underline{H}_2$); 3.18-3.36 (m, 4H, N1HCH$_2$CH$_2$C$\underline{H}_2$, C$\underline{H}_2$CH$_2$CH$_2$N9'H); 3.02-3.15 (m, 2H, NHCH$_2$C$\underline{H}_2$NH); 2.87-3.01 (m, 2H, NHC$\underline{H}_2$CH$_2$NH); 1.99-2.20 (m, 4H, N1HCH$_2$C$\underline{H}_2$CH$_2$, CH$_2$C$\underline{H}_2$CH$_2$ N$^{9'}$H).

EXAMPLE 23

Preparation of dimer IIa (C-2025): 11-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl. A mixture of derivative 5b (0.001 mol), 5 ml phenol and 9-phenoxy-4-methyl-1-niroacridine (3b) (0.001 mol) was stirred at 140° C. for 3.5 h. After cooling, the reaction mixture was dissolved in methanol (~10 ml), and then poured into diethyl ether (~100 ml) and then stirred for 0.5 h. The precipitate was filtered off, washed with ether and then with acetone. The product was dissolved in methanol and small quantity of silica gel was added and solvent was evaporated. The remainder was loaded onto a dry chromatography column. The initial eluent was CHCl$_3$ and then CHCl$_3$/MeOH at a ratio of (15:1, 10:1 v/v), CHCl$_3$/MeOH/ NH$_3$ (10:1:0.1 v/v/v). Yield 36%, m.p. 208-210° C. Elemental analysis: C$_{38}$H$_{42}$N$_8$O$_4$Cl$_4$×5H$_2$O. $^1$H NMR (Me$_2$SO-d$_6$+ TFA) δ: 10.23 (s, 1H, N10C$\underline{H}$); 9.17 (br.s, 1H, N1$\underline{H}$CH$_2$); 8.40-8.46 (m, 1H, C8'); 8.32 (d, J=9.0 Hz, 1H, C3); 8.20 (d, J=8.7 Hz, 1H, C5'); 8.15 (d, J=7.8 Hz, 1H, C2'); 8.07 (d, J=9.3 Hz, 1H, C6'); 7.96 (t, J=7.8 Hz, 1H, C3'); 7.86 (d, J=7.8 Hz, 1H, C5); 7.75 (s, 1H, C8); 7.55-7.64 (m, 1H, C7'); 7.36-7.43 (m, 1H, C6); 7.18 (d, J=9.3 Hz, 1H, C2); 3.32-3.94 (m, 12H, Alif-H) 3.23-3.33 (m, 2H, Alif-H); 3.10-3.15 (m, 2H, Alif-H); 2.75 (s, 3H, Ar—CH$_3$); 2.03-2.22 (m, 4H, N5HCH$_2$C$\underline{H}_2$CH$_2$, CH$_2$C$\underline{H}_2$CH$_2$ N9'H).

Preparation of derivative 5b: 1-(Aminopropyl)-4[N-5-(8-hydroxy-imidazo[4,5,1-de]-acridin-6-on)-3-aminopropyl]piperazine×4HCl. The previously obtained derivative 2b (0.0027 mol), 10% Pd/C (catalytic quantities) and 40 ml 96% formic acid were hydrogenated by passing gaseous hydrogen through them at room temperature for 24 hours. After this time, the catalyst was filtered off, and to the filtrate was added 2-3 ml concentrated HCl and the mixture was heated at 110° C. for 24 h. The formic acid was evaporated, and the resulting remainder was heated for 3 h in a water-methanol mixture at a ratio of 1/1 (about 50 ml). The solvent was evaporated, the remainder was dissolved in methanol and acidified with concentrated hydrochloric acid. The product was crystallized from acetone. Yield 78%.

EXAMPLE 24

Preparation of dimer IIb (C-2027): 1-[3-(8-hydroxy-imidazo[4,5,1-de]-acridin-6-on-5-yl)aminopropyl]-4-[3'-(1'-nitroacridin-1-yl)-aminopropyl]piperazine×3HCl The method of synthesis and purification the product was similar to that in the case of derivative IIa: 5b and 3a were used; the reaction temperature—90° C., the time was 24 h, yield 63%, m.p. 231-232° C. Elemental analysis: $C_{37}H_{39}N_8O_4Cl_3\times 3H_2O$. $^1H$ NMR (Me$_2$SO-d$_6$+TFA) δ: 10.15 (s, 1H, N10 C$\underline{H}$); 8.50 (br.s, 1H, C8'); 8.33 (d, J=8.8 Hz, 1H, C3); 8.22 (d, J=7.4 Hz, 1H, C5'); 8.14 (d, J=8.8 Hz, 1H, C2'); 7.95-8.05 (m, 2H, C6', C3'); 7.87 (d, J=8.2 Hz, 1H, C5); 7.74 (s, 1H, C8); 7.61 (d, J=7.6 Hz, 1H, C7'); 7.40 (dd, J$_1$=8.7 Hz, J$_2$=2.3 Hz, 1H, C6); 7.16 (d, J=9.1 Hz, 1H, C2); 3.52-3.80 (m, 10H, Alif-H) 3.33-3.52 (m, 2H, C$\underline{H}_2$N(CH$_2$CH$_2$)$_2$NCH$_2$); 3.20-3.33 (m, 2H N(C$\underline{H}_2$CH$_2$)$_2$N); 3.04-3.19 (m, N(CH$_2$C$\underline{H}_2$)$_2$NC); 2.14-2.23 (m, 2H, CH$_2$C$\underline{H}_2$CH$_2$ N9'H); 2.05-2.14 (m, 2H, N5HCH$_2$C$\underline{H}_2$CH$_2$)

EXAMPLE 25

Preparation of dimer IIc (C-2028): 9-{N-[(imidazo[4,5,1-de]-acridin-6-on-5-yl)aminopropyl]-N-methylaminopropylamino}-1'-nitroacridine×1.5HCl. The method of synthesis and purification the product was similar to that in the case of derivative IIb: 5a and 3a were used; the reaction temperature—90° C., the time was 24 h, yield 45%, m.p. 207-209° C. Elemental analysis: $C_{34}H_{34}N_7O_3Cl_{1.5}\times 2H_2O$. $^1H$ NMR (Me$_2$SO-d$_6$+TFA) δ: 9.79 (s, 1H, N10C$\underline{H}$); 9.70 (br.s, 1H, N1$\underline{H}$CH$_2$); 8.43 (d, J=8.3 Hz, 1H, Ar—H); 8.37-8.41 (m, 1H, Ar—H); 8.36 (d, J=7.8 Hz, 1H, Ar—H); 8.20 (d, J=7.3 Hz, 1H, Ar—H); 8.08 (d, J=8.8 Hz, 1H, Ar—H); 7.99-8.02 (m, 2H, Ar—H); 7.92-7.99 (m, 2H, Ar—H); 7.82 (d, J=8.8 Hz, 1H, Ar—H); 7.63 (t, J=7.6 Hz, 1H, Ar—H); 7.58 (t, J=7.3 Hz, 1H, Ar—H); 7.01 (d, J=9.3 Hz, 1H, C2); 3.58-3.63 (m, 2H, CH$_2$N9'H) 3.48-3.56 (m, 2H, CH$_2$NSH); 2.91-3.27 (m, 4H, C$\underline{H}_2$NCH$_3$C$\underline{H}_2$); 2.75 (s, 3H, NCH$_3$); 1.90-2.22 (m, 4H, CH$_2$C$\underline{H}_2$CH$_2$N9'H; N$^5$HCH$_2$C$\underline{H}_2$CH$_2$). Preparation of derivative 5c: 5-{3-[N-(3-Aminopropyl)-N-methylamino]propylamino}-imidazo[4,5,1-de]-acridin-6-one×2HCl. The method of synthesis was similar to that in the case of derivative 5b: derivative 2i was used; yield 74%.

EXAMPLE 26

Preparation of dimer IId (C-2037): 9-[N-(imidazo[4,5,1-de]-acridin-6-on)-aminoethylaminoethylamino-ethylamino]-4'-methyl-1'-nitroacridine×4HCl. The method of synthesis and purification the product was similar to that in the case of derivative Hb: 5e and 3a were used; the reaction temperature—90° C., the time was 3 h, yield 27%, m.p. 220-221° C. Elemental analysis: $C_{33}H_{34}N_8O_3Cl_4\times 5H_2O$. $^1H$ NMR (Me$_2$SO-d$_6$+TFA) δ: 10.13 (s, 1H, NlOCH); 9.18 (br.s, 1H, N1$\underline{H}$CH$_2$); 8.52 (d, J=8.3 Hz, 1H, C8); 8.46 (d, J=8.3 Hz, 1H, C8'); 8.40 (d, J=7.8 Hz, 1H, C5'); 8.20 (d, J=7.8 Hz, 1H, C2'); 8.13 (d, J=8.8 Hz, 1H, C4'); 8.07 (d, 1H, C3); 8.01 (t, 1H, C3'); 7.91-7.98 (m, 2H, C7', C6); 7.85 (d, J=8.3 Hz, 1H, C5); 7.66 (t, J=7.8 Hz, 1H, C6'); 7.55-7.63 (t, 1H, C7); 7.16 (d, J=9.3 Hz, 1H, C2); 3.85-3.94 (m, 2H, C$\underline{H}_2$N9'H) 3.77-3.85 (m, 2H, C$\underline{H}_2$NSH); 3.36-3.43 (m, 2H, $\overline{N}$HC$\underline{H}_2$CH$_2$N9'H); 3.17-3.27 (m, 6H, N5HCH$_2$C$\underline{H}_2$NHC$\underline{H}_2$C$\underline{H}_2$NH). Preparation of derivative 5e: 5-{2-[2-(2-Aminoethylamino)-ethylamino]-ethylamino}-imidazo[4,5,1-de]-acridin-6-on×4HCl. The method of synthesis was similar to that in the case of derivative 5b: derivative 2k was used; yield 67%.

EXAMPLE 27

Preparation of dimer IIe (C-2041): 1-[3-(imidazo[4,5,1-de]-acridin-6-on-5-yl)aminopropyl]-4-[3'-(1'-nitroacridin-1-yl)-aminopropyl]piperazine×4HCl. The method of synthesis and purification the product was similar to that in the case of derivative 5d and 3a were used; the reaction temperature—90° C., the time was 19 h, yield 56%, m.p. 199-201° C. Elemental analysis: $C_{37}H_{40}N_8O_3Cl_4\times 6H_2O$. $^1H$ NMR (Me$_2$SO-d$_6$+TFA) δ: 13.79 (br.s, 1H, N10'-$\underline{H}^+$); 9.81 (s, 1H, N10C$\underline{H}$); 8.48-8.54 (m, 1H, Ar—H); 8.46 (d, J=8.3 Hz, 1H, Ar—H); 8.40 (d, J=7.8 Hz, 1H, Ar—H); 8.22 (d, J=7.3 Hz, 1H, Ar—H); 8.13 (d, J=8.3 Hz, 1H, Ar—H); 8.02-8.09 (m, 2H, Ar—H); 7.94-8.01 (m, 2H, Ar—H); 7.86 (d, J=8.3 Hz, 1H, Ar—H); 7.66 (t, 1H, Ar—H); 7.59 (t, 1H, Ar—H); 7.06 (d, J=9.3 Hz, 1H, C2); 3.61-3.73 (m, 4H, N5HC$\underline{H}_2$, C$\underline{H}_2$N9'H); 3.50-3.59 (m, 4H, C$\underline{H}_2$N(CH$_2$CH$_2$)$_2$NC$\underline{H}_2$); 3.24-3.33 (m, 4H, N(C$\underline{H}_2$C$\underline{H}_2$)$_2$N); 3.06-3.16 (m, 4H, N(CH$_2$C$\underline{H}_2$)$_2$N); 2.05-2.21 (m, 4H, N5HCH$_2$C$\underline{H}_2$CH$_2$, CH$_2$C$\underline{H}_2$CH$_2$N9'H). Preparation of derivative 5d: 1-(Aminopropyl)-4[N-5-(imidazo[4,5,1-de]-acridin-6-on)-3-aminopropyl]piperazine×4HCl. The method of synthesis was similar to that in the case of derivative 5b: derivative 2j was used; yield 72%.

EXAMPLE 28

Preparation of dimer IIf (C-2042): 9-{N-[(8-hydroxyimidazo[4,5,1-de]-acridin-6-on-5-yl)aminopropyl]-N-methylaminopropylamino}-1'-nitroacridine×3HCl. The method of synthesis and purification the product was similar to that in the case of derivative 5a and 3a were used; the reaction temperature—90° C., the time was 26 h, yield 42%, m.p. 223-225° C. Elemental analysis: $C_{34}H_{37}N_7O_4Cl_3\times 4H_2O$. $^1H$ NMR (Me$_2$SO-d$_6$+TFA) δ: 10.28 (br.s, 1H, N1$\underline{H}$CH$_2$); 10.13 (s, 1H, N10C$\underline{H}$); 8.39-8.52 (m, 1H, C8'); 8.31 (d, J=9.3 Hz, 1H, C3); 8.20 (d, J=7.3 Hz, 1H, C5'); 8.12 (d, J=8.8 Hz, 1H, C2'); 8.05 (d, J=9.3 Hz, 1H, Ar—H) 7.98-8.03 (m, 1H, Ar—H); 7.92-7.98 (m, 1H, C5); 7.85 (d, J=8.8 Hz, 1H, Ar—H); 7.71 (s, 1H, C8); 7.52-761 (m, 1H, C7'); 7.40 (d, J=8.8 Hz, 1H, C6); 7.13 (d, J=9.3 Hz, 1H, C2); 3.58-3.71 (m, 2H, CH$_2$N9'H) 3.51-3.58 (m, 2H, N5HCH$_2$); 3.23-3.33 (m, 4H, C$\underline{H}_2$NCH$_3$C$\underline{H}_2$); 2.70 (s, 3H, NCH$_3$); 2.08-2.19 (m, 2H, CH$_2$C$\underline{H}_2$CH$_2$N9'H); 2.00-2.08 (m, 2H, N5HCH$_2$C$\underline{H}_2$CH$_2$). Preparation of derivative 5a: 5-{3-[N-(3-Aminopropyl)-N-methylamino]propylamino}-8-hydroxy-imidazo[4,5,1-de]-acridin-6-on×3HCl. The method of synthesis was similar to that in the case of derivative 5b: derivative 2a was used; yield 67%.

EXAMPLE 29

Preparation of dimer IIg (C-2045): 9-{N-[(8-hydroxyimidazo[4,5,1-de]-acridin-6-on-5-yl)aminopropyl]-N-methylaminopropylamino}-4'-methyl-1'-nitroacridine×3HCl. The method of synthesis and purification the product was similar to that in the case of derivative IIb: 5a and 3b were used; the reaction temperature—90° C., the time was 26 h, yield 45%, m.p. 218-218° C. Elemental analysis: $C_{35}H_{36}N_7O_4Cl_3 \times 4H_2O$. $^1H$ NMR (Me$_2$SO-d$_6$+TFA) δ: 10.03 (s, 1H, N10C H); 9.07 (br.s, 1H, N1HCH$_2$); 8.44 (m, 1H, C8'); 8.31 (d, J=8.8 Hz, 1H, C3); 8.22 (d, J=8.3 Hz, 1H, C5'); 8.15 (d, J=7.8 Hz, 1H, C2'); 8.04 (d, J=9.3 Hz, 1H, C6'); 7.96 (t, J=7.8 Hz, 1H, C3'); 7.87 (d, J=7.3 Hz, 1H, C5); 7.70 (s, 1H, C8); 7.54-7.63 (m, 1H, C7'); 7.39 (dd, J$_1$=8.8 Hz, J$_2$=2.4 Hz, 1H, C6); 7.10 (d, J=8.8 Hz, 1H, C2); 3.44-3.67 (m, 4H, CH$_2$N9'H, N5HCH$_2$) 2.91-3.27 (m, 4H, CH$_2$NCH$_3$CH$_2$); 2.76 (s, 3H, Ar—CH$_3$); 2.70 (s, 3H, NCH$_3$); 2.12-2.23 (m, 2H, CH$_2$CH$_2$CH$_2$ N9'H) 1.98-2.12 (m, 2H, N1HCH$_2$C H$_2$CH$_2$)

EXAMPLE 30

Preparation of dimer IIh (C-2049): 1-[3-(8-methoxy-imidazo[4,5,1-de]-acridin-6-on-5-yl)aminopropyl]-4-[3'-(1'-nitroacridin-1-yl)-aminopropyl]piperazine×4HCl The method of synthesis and purification the product was similar to that in the case of derivative IIb: 5g and 3a were used; the reaction temperature—90° C., the time was 7h, yield 51%, m.p. 218-220° C. Elemental analysis: $C_{38}H_{42}N_8O_4Cl_4 \times 4H_2O$. $^1H$ NMR (Me$_2$SO-d$_6$+TFA) δ: 10.30 (s, 1H, N10HCH); 8.43 (d, J=9.1 Hz, 1H, Ar—H); 8.18 (d, J=7.7 Hz, 1H, C5'); 8.04-8.07 (m, 2H, Ar—H); 7.90-8.01 (m, 2H, Ar—H); 7.79-7.84 (m, 2H, C8); 7.53-7.62 (m, 2H, Ar—H); 7.18 (d, J=9.3 Hz, 1H, C2); 2.89 (s, 3H, OCH$_3$); 3.55-3.69 (m, 10H, Alif-H) 3.26-3.34 (m, 4H N(C H$_2$CH$_2$)$_2$N); 3.06-3.19 (m, 2H, N(CH$_2$CH$_2$)$_2$NCH$_2$); 2.04-2.20 (m, 4H, CH$_2$CH$_2$CH$_2$N9'H; N1HCH$_2$CH$_2$CH$_2$). Preparation of derivative5g: 1-(Aminopropyl)-4 [N-5-(8-methoxy-imidazo[4,5,1-de]-acridin-6-on)-3-aminopropyl] piperazine×4HCl. A mixture of 1-chloro-7-methoxy-4-nitro-9(10H)-acridone (1d) (4.57 g, 0.015 mol), 1,4-Bis-(3-aminopropyl)piperazine (12 g, 0.06 mol) in DMSO (25 ml) was stirred at 60° C. for 0.5 h. After this time, water was added (~200 ml) and then stirred for 0.5 h. The precipitate was filtered off suspended in water, acidified with a dilute hydrochloric acid and stirred again for 0.5 h. Undissolved material was separated by filtration, and the filtrate was evaporated to a smaller volume. The product (2m) was precipitated out using acetone (~100 ml), and then was filtered off. Yield 43%. The resulting derivative 2m (0.002 mol), 10% Pd/C (catalytic quantities) and 30 ml 96% of formic acid were hydrogenated by passing gaseous hydrogen through them at room temperature for 24 hours. After this time, the catalyst was filtered off, and to the filtrate was added about 2-3 ml concentrated HCl and the mixture was heated at a temperature of 110° C. for 24 h. The formic acid was evaporated, and the resulting remainder was heated for 3 h in a water-methanol mixture at a ratio of 1/1 (about 50 ml). The solvent was evaporated, the remainder was dissolved in methanol and acidified with concentrated hydrochloric acid. The product was crystallized from methanol/acetone. Yield 59%.

EXAMPLE 31

Preparation of dimer IIi (C-2050): 1-[3-(imidazo[4,5,1-de]-acridin-6-on-5-yl)aminopropyl]-4-[3'-(4'-methyl-1'-nitroacridin-1-yl)-aminopropyl]piperazine×4HCl The method of synthesis and purification the product was similar to that in the case of derivative IIb: 5d and 3b were used; the reaction temperature—140° C., the time was 7 h, Yield 23%, m.p. 218-220° C. Elemental analysis: $C_{38}H_{42}N_8O_3Cl_4 \times 7H_2O$. $^1H$ NMR (Me$_2$SO-d$_6$+TFA) δ: 10.16 (s, 1H, N10C H); 8.47 (d, 1H, Ar—H); 8.40 (d, 2H, Ar—H); 8.19 (d, J=7.3 Hz, 1H, Ar—H); 8.15 (d, J=8.3 Hz, 1H, Ar—H); 8.07 (d, 2H, Ar—H); 7.92-7.98 (m, 2H, Ar—H); 7.85 (d, J=8.3 Hz, 1H, Ar—H); 7.67 (t, 1H, Ar—H); 7.59 (t, 1H, Ar—H); 7.13 (d, J=9.3 Hz, 1H, C2); 3.49-3.67 (m, 10H, Alif-H) 3.23-3.36 (m, 4H, N(CH$_2$CH$_2$)$_2$N); 3.04-3.20 (m, 2H, N(CH$_2$CH$_2$)$_2$N); 2.74 (s, 3H, Ar—CH$_3$); 2.03-2.21 (m, 4H, N5HCH$_2$C H$_2$CH$_2$, CH$_2$CH$_2$CH$_2$ N9'H)

EXAMPLE 32

Preparation of dimer IIj (C-2051): 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl. The method of synthesis and purification the product was similar to that in the case of derivative IIb: 5f and 3a were used; the reaction temperature ~90° C., the time was 6h, Yield 20%, m.p. 238-240° C. Elemental analysis: $C_{38}H_{42}N_8O_4Cl_4 \times 8H_2O$. $^1H$ NMR (Me$_2$SO-d$_6$+TFA) δ: 8.40-8.48 (m, 1H, Ar—H); 8.15-8.22 (m, 2H, Ar—H); 8.06-8.11 (d, 1H, Ar—H); 7.92-8.03 (m, 3H, Ar—H); 7.83 (s, 1H, C8) 7.82-7.85 (m, 1H, C7'); 7.58 (t, 1H, Ar—H); 7.38 (dd, 1H, Ar—H); 7.13 (d, 1H, C2); 3.60-3.69 (m, 6H, NSHCH$_2$, C H$_2$N9'H, CH$_2$N(CH$_2$CH$_2$)$_2$N) 3.53-3.60 (m, 4H, N(CH$_2$C H$_2$)$_2$N); 3.27-3.33 (m, 4H, N(CH$_2$CH$_2$)$_2$N); 3.24 (s, 3H, imidazo-CH$_3$); 3.08-3.17 (m, 2H, N(CH$_2$CH$_2$)$_2$NCH$_2$); 2.12-2.19 (m, 2H, CH$_2$CH$_2$CH$_2$ N9'H); 2.04-2.12 (m, N5HCH$_2$CH$_2$CH$_2$). Preparation of derivative 5f: 1-(Aminopropyl)-4[N-5-(8-hydroxy-methylimidazo[4,5,1-de]-acridin-6-on)-3-aminopropyl]piperazine×4HCl. The previously obtained derivative 2b (0.004 moles), 10% Pd/C (catalytic quantities) in 150 ml (4:1) of the mixture MeOH:H$_2$O, were hydrogenated by passing gaseous hydrogen through them at room temperature for 24 hours. After this time, the catalyst was filtered off into an acidified solution of HO/diethyl ether. The precipitate was collected by filtration, and was diluted in 40 ml DMA and heated for 24 h. Next, the DMA was evaporated off to 1/3 volume, the precipitate was filtered off and acetone was added to the filtrate. The precipitates was dissolved in methanol and acidified with concentrated hydrochloric acid. The product was crystallized from acetone. Yield 31%.

EXAMPLE 33

Preparation of dimer IIk (C-2053): 9-{N-[(imidazo[4,5,1-de]-acridin-6-on-5-yl)aminopropyl]-N-methylaminopropylamino}-4'-methyl-1'-nitroacridine×3HCl. The method of synthesis and purification the product was similar to that in the case of derivative IIa: 5c and 3b were used; the reaction temperature~120° C., the time was 3 h, yield 40%, m.p. 205-206° C. Elemental analysis: $C_{35}H_{36}N_7O_3Cl_3 \times 2H_2O$. $^1H$ NMR (Me$_2$SO-d$_6$+TFA) δ: 9.93 (br.s, 1H, N1HCH$_2$); 9.77 (br.s, 1H, N10CH); 8.44 (d, J=8.3 Hz, 1H, Ar—H); 8.36 (d, J=7.3 Hz, 2H, Ar—H); 8.18 (d, J=8.8 Hz, 1H, C3); 8.15 (d, J=7.8 Hz, 1H, Ar—H); 8.04 (d, J=9.3 Hz, 1H, Ar—H); 7.97 (t, J=7.8 Hz, 2H, Ar—H); 7.88 (d, J=7.8 Hz, 1H, Ar—H); 7.64 (t, J=7.6 Hz, 1H, Ar—H); 7.55-7.61 (m, 1H, Ar—H); 7.02 (d, J=8.8 Hz, 1H, C2); 3.42-3.61 (m, 4H, CH$_2$N9'H, N5HCH$_2$) 3.07-3.24 (m, 4H, CH$_2$NCH$_3$CH$_2$); 2.75 (s, 3H, Ar—CH$_3$); 2.73 (s, 3H, NCH$_3$); 1.95-2.20 (m, 4H, N5HCH$_2$CH$_2$CH$_2$, CH$_2$CH$_2$CH$_2$ N9'H).

EXAMPLE 34

Preparation of dimer IIIa (C-2047): 1-[3-(8-hydroxy-6H-[1,2,3]triazolo[4,5,1-de]-acridin-6-on-5-yl)aminopropyl]-4-

[3'-(1'-nitroacridin-1-yl)-aminopropyl]piperazine×4HCl. The method of synthesis and purification the product was similar to that in the case of derivative IIa: 7a and 3a were used; the reaction temperature –90° C., the time was 6 h, yield 59%, m.p. 217-219° C. Elemental analysis: $C_{36}H_{39}N_9O_4Cl_4 \times 5H_2O$. $^1H$ NMR (Me$_2$SO-d$_6$+TFA) δ: 9.32 (br.s, 1H, N5$\underline{H}$CH$_2$); 8.53 (m, 1H, C8'); 8.30 (d, J=8.8 Hz, 1H, C10); 8.26 (d, J=9.3 Hz, 1H C3); 8.21 (d, J=7.3 Hz, 1H, C2'); 8.18 (d, J=8.8 Hz, 1H, C5'); 8.02 (t, J=8.1 Hz, 1H, C3'); 7.94-7.99 (m, 1H, C6'); 7.90 (d, J=8.3 Hz, 1H, C4'); 7.71 (s, 1H, C7); 7.60 (t, J=7.6 Hz, 1H, C7'); 7.40 (dd, J$_1$=8.8 Hz, J$_2$=2.9 Hz, 1H, C9); 7.17 (d, J=9.3 Hz, 1H, C4); 3.72-3.90 (m, 2H, C$\underline{H}_2$N9'H); 3.57-3.72 (m, 6H, N5HC$\underline{H}_2$, C$\underline{H}_2$N(CH$_2$CH$_2$)$_2$NC$\underline{H}_2$); 3.36-3.54 (m, 4H, N(C$\underline{H}_2$C$\underline{H}_2$)$_2$N); 3.22-3.32 (m, 2H, N(C$\underline{H}_2$CH$_2$)$_2$N); 3.04-3.18 (m, 2H, N(C$\underline{H}_2$CH$_2$)$_2$N); 2.16-2.24 (m, 2H, CH$_2$C$\underline{H}_2$CH$_2$N9'H) 2.06-2.16 (m, 2H, N5HCH$_2$C$\underline{H}_2$CH$_2$). Preparation of derivative 7a: 1-(Aminopropyl)-4[N-5-(8-hydroxy-6H-[1,2,3]triazolo[4,5,1-de]-acridin-6-on)-3-aminopropyl]piperazine×4HCl. A mixture of 1,4-Bis-(3-amionopropyl)piperazine (2.7 g, 0.0135 mol), 6a (1.16 g, 0.0045 mol) in DMA (10 ml) (compound 6a we obtained using an analogous method to as in Cholody et al.; *J. Med. Chem.*, 1990, 33, 10, 2852-2856), was heated at 60° C. for 4 h. After this time, methanol was added and the reaction mixture was left overnight in the refrigerator. The precipitate was filtered off and then dissolved in chloroform, acidified with HCl/diethyl ether and was precipitated out with diethyl ether. The product was crystallized from methanol/acetone. Yield 65%.

EXAMPLE 35

Preparation of dimer IIIb (C-2048): 1-[3-(6H-[1,2,3]triazolo[4,5,1-de]-acridin-6-on-5-yl)aminopropyl]-4-[3'-(1'-nitroacridin-1-yl)-aminopropyl]piperazine×4HCl. The method of synthesis and purification the product was similar to that in the case of derivative IIIa: 7b and 3a were used; the reaction temperature—90° C., the time was 1.5h, yield 66%, m.p. 223-225° C. Elemental analysis: $C_{36}H_{39}N_9O_3Cl_4 \times 3H_2O$. $^1H$ NMR (Me$_2$SO-d$_6$+TFA) δ: 9.35 (br.s, 1H, N5$\underline{H}$CH$_2$); 8.50-8.56 (m, 1H, C8'); 8.48 (d, J=8.3 Hz, 1H, C10); 8.39 (d, J=7.8 Hz, 1H, C7); 8.32 (d, J=9.3 Hz, 1H, C3); 8.22 (d, J=7.8 Hz, 1H, C2'); 8.16 (d, J=8.8 Hz, 1H, C5'); 7.95-8.07 (m, 3H, C6', C3', C8); 7.89 (d, J=8.3 Hz, 1H, C4'); 7.69 (t, J=7.6 Hz; 1H, C9); 7.61 (t, J=7.6 Hz, 1H, C7'); 7.22 (d, J=9.3 Hz, 1H, C4); 3.55-3.92 (m, 8H, C$\underline{H}_2$N9'H, N5HC$\underline{H}_2$, C$\underline{H}_2$N(CH$_2$CH$_2$)$_2$NC$\underline{H}_2$); 3.36-3.54 (m, 4H, N(C$\underline{H}_2$C$\underline{H}_2$)$_2$N); 3.33-3.51 (m, 4H, N(C$\underline{H}_2$CH$_2$)$_2$N); 3.21-3.32 (m, 2H); 3.01-3.21 (m, 2H); 2.01-2.27 (m, 4H, CH$_2$C$\underline{H}_2$CH$_2$N9'H; N5HCH$_2$C$\underline{H}_2$CH$_2$). Preparation of derivative 7b: 1-(Aminopropyl)-4[N-5-(6H-[1,2,3]triazolo [4,5,1-de]acridin-6-on)-3-aminopropyl]piperazine×4HCl. The method of synthesis was similar to that in the case of derivative 7a: 6b and 1,4-bis(3-N-aminopropyl)-piperazine were used. Chloroform was added to the reaction mixture and washed with water. The aqueous phase was evaporated, dissolved in methanol, acidified with HCl/diethyl ether, and then was precipitated out as hydrochloride with diethyl ether; yield 72%.

EXAMPLE 36

Preparation of dimer IIIc (C-2052): 9-{N-[(8-hydroxy-6H-[1,2,3]triazolo[4,5,1-de]-acridin-6-on-5-yl)aminopropyl]-N-methylaminopropylamino}-1'-nitroacridine×2CH$_3$SO$_2$OH. The method of synthesis and purification the product was similar to that in the case of derivative IIIa: 7c and 3a were used; the reaction temperature—90° C., the time was 2 h, yield 40%, m.p. 195-197° C. Elemental analysis: $C_{35}H_{38}N_8O_{10}S_2 \times 3H_2O$. $^1H$ NMR (Me$_2$SO-d$_6$+TFA) δ: 10.60 (br.s, 1H, OH); 9.34 (br.s, 1H, N5$\underline{H}$CH$_2$); 8.36-8.42 (m, 1H, C8'); 8.20 (d, J=8.8 Hz, 1H, C10); 8.28 (d, J=9.3 Hz, 1H C3); 8.18-8.22 (m, 1H, C2'); 8.09 (d, J=8.3 Hz, 1H, C5'); 8.00-8.05 (m, 1H, C3'); 7.50-8.00 (m, 1H, C6'); 7.83 (d, J=8.3 Hz, 1H, C4'); 7.69 (s, 1H, C7); 7.56-7.62 (m, 1H, C7'); 7.41 (dd, J$_1$=8.8 Hz, J$_2$=2.9 Hz, 1H, C9); 7.16 (d, J=9.3 Hz, 1H, C4); 3.58-3.64 (m, 4H, C$\underline{H}_2$N5,9'H); 2.93-3.21 (m, 4H, C$\underline{H}_2$NCH$_3$C$\underline{H}_2$); 2.73 (s, 3H, NCH$_3$); 2.00-2.16 (m, 4H, C$\underline{H}_2$CH$_2$CH$_2$N9'H; N5HCH$_2$C$\underline{H}_2$CH$_2$). Preparation of derivative 7c: 5-[3-[N-(3-Aminopropyl)-N-methylamino]propylamino]-8-hydroxy-6H-[1,2,3]triazolo[4,5,1-de]-acridin-6-one×4HCl. The method of synthesis was similar to that in the case of derivative 7a: 6a and 3,3-diamino-N-methyldipropylamine were used; yield 67%.

EXAMPLE 37

Preparation of dimer IIId (C-2056): 9-{N-5-[(8-hydroxy-6H-[1,2, 3]triazolo[4,5,1-de]-acridin-6-on-5-yl)aminopropyl]-N-methylaminopropylamino}-4'-methyl-1'-nitroacridine×3HCl. The method of synthesis and purification the product was similar to that in the case of derivative IIIa 7c and 3b were used; the reaction temperature—100° C., the time was 1 h, yield 35%, m.p. 205-207° C. Elemental analysis: $C_{34}H_{35}N_8O_4Cl_3 \times 2H_2O$. $^1H$ NMR (Me$_2$SO-d$_6$+TFA) δ: 10.91 (s, 1H, OH); 9.32 (t, 1H, N5H); 8.40-8.60 (m, 1H, C8'); 8.31 (d, J=8.8 Hz, 1H, C10); 8.27 (d, J=9.3 Hz, 1H, C3); 8.16 (d, J=8.3 Hz, 1H, C5'); 8.07 (d, J=7.8 Hz, 1H, C2'); 7.94 (t, J=7.8 Hz, 1H, C6'); 7.83 (d, J=7.8 Hz, 1H, C3'); 7.70 (s, 1H, C7); 7.53-7.63 (m, 1H, C7'); 7.42 (dd, J$_1$=8.8 Hz, J$_2$=2.9 Hz, 1H, C9); 7.17 (d, J=9.3 Hz, 1H, C4); 3.52-3.71 (m, 4H, C$\underline{H}_2$N5,9'-H); 2.97-3.17 (m, 4H, C$\underline{H}_2$NCH$_3$C$\underline{H}_2$); 2.77 (s, 3H, CH$_3$-Ar); 2.67 (s, 3H, NCH$_3$); 2.12-2.23 (m, 4H, CH$_2$C$\underline{H}_2$CH$_2$ N9'H; N5HCH$_2$C$\underline{H}_2$CH$_2$).

EXAMPLE 38

Preparation of dimer IIIe (C-2057): 1-[3-(8-hydroxy-6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl. The method of synthesis and purification the product was similar to that in the case of derivative IIIa: 7a and 3b were used; the reaction temperature of 100° C., the time was 1.5 h, yield 39%, m.p. 225-227° C. Elemental analysis: $C_{37}H_{41}N_9O_4Cl_4 \times 3H_2O$. $^1H$ NMR (Me$_2$SO-d$_6$+TFA) δ: 9.37 (t, 1H, N5H); 8.38-8.48 (m, 1H, C8'); 8.33 (d, J=8.8 Hz, 1H, C10); 8.29 (d, J=9.3 Hz, 1H, C3); 8.20 (d, J=8.3 Hz, 1H, C5'); 8.16 (d, J=7.8 Hz, 1H, C2'); 7.97 (t, J=7.8 Hz, 1H, C6'); 7.88 (d, J=7.8 Hz, 1H, C3'); 7.73 (s, 1H, C7); 7.58-7.65 (m, 1H, C7'); 7.41 (dd, J$_1$=8.8 Hz, J$_2$=2.9 Hz, 1H, C9); 7.19 (d, J=9.3 Hz, 1H, C4); 3.22-3.79 (m, 12H, C$\underline{H}_2$N5,9'-H, N(C$\underline{H}_2$C$\underline{H}_2$)$_2$N); 2.97-3.17 (m, 4H, C$\underline{H}_2$N(CH$_2$C$\underline{H}_2$)$_2$NC$\underline{H}_2$); 2.77 (s, 3H, Ar—CH$_3$); 2.12-2.23 (m, 4H, CH$_2$C$\underline{H}_2$CH$_2$ N9'H; N5HCH$_2$C$\underline{H}_2$CH$_2$).

EXAMPLE 39

Preparation of dimer IIIf (C-2058): 1-[3-(6H-[1,2,3]triazolo[4,5,1-de]-acridin-6-on-5-yl)aminopropyl]-4l-[3'-(4'-methyl-1'-nitroacridin-1-yl)-aminopropyl]piperazine×4HCl. The method of synthesis and purification the product was similar to that in the case of derivative IIIa: 7b and 3b were used; the reaction temperature—100° C., the time was 1h, yield 35%, m.p. 192-193° C. Elemental analysis:

$C_{37}H_{41}N_9O_3Cl_4 \times 2H_2O$. $^1$H NMR (Me$_2$SO-d$_6$+TFA) δ: 9.37 (t, 1H, N5H); 8.53 (d, J=7.8 Hz, 1H, C10); 8.46-8.50 (m, 1H, C8'); 8.43 (d, J=7.3 Hz, 1H, C7); 8.36 (d, J=9.3 Hz, 1H, C3); 8.26 (d, J=8.3 Hz, 1H, C5'); 8.20 (d, J=7.3 Hz, 1H, C2'); 7.95-8.06 (m, 2H, C6', C8); 7.93 (d, J=7.3 Hz, 1H, C3'); 7.72 (t, J=7.3 Hz, 1H, C9); 7.62-7.68 (m, 1H, C7'); 7.25 (d, J=9.3 Hz, 1H, C4); 3.41-3.78 (m, 12H, CH$_2$N5,9'-H, N(CH$_2$CH$_2$)$_2$N); 3.05-3.39 (m, 4H, CH$_2$N(CH$_2$CH$_2$)$_2$NCH$_2$); 2.80 (s, 3H, CH$_3$-Ar); 2.04-2.22 (m, 4H, CH$_2$CH$_2$CH$_2$ N9'H; N$^5$HCH$_2$CH$_2$CH$_2$).

EXAMPLE 40

Preparation of dimer IIIg (C-2059): 9-{N-5-[(6H-[1,2,3]triazolo[4,5,1-de]-acridin-6-on-5-yl)aminopropyl]-N-methylaminopropylamino}-1'-nitroacridine×3HCl. The method of synthesis and purification the product was similar to that in the case of derivative IIIa: 7d and 3a were used; the reaction temperature—90° C., the time was 1.5 h, yield 46%, m.p. 189-191° C. Elemental analysis: $C_{33}H_{33}N_8O_3Cl_3 \times 3H_2O$. $^1$H NMR (Me$_2$SO-d$_6$+TFA) δ: 9.30 (t, 1H, N5H); 8.48-8.54 (m, 1H, C8'); 8.47 (d, J=8.3 Hz, 1H, C10); 8.36 (d, J=7.8 Hz, 1H, C7); 8.28 (d, J=9.3 Hz, 1H, C3); 8.19 (d, J=7.8 Hz, 1H, C2'); 8.16 (d, J=8.8 Hz, 1H, C5'); 7.94-8.02 (m, 2H, C3', C6'); 7.90-7.96 (m, 1H, C8); 7.88 (d, J=8.3 Hz, 1H, C4'); 7.66 (t, J=7.8 Hz, 1H, C9); 7.58 (t, J=7.8 Hz, 1H, C7'); 7.18 (d, J=9.3 Hz, 1H, C4); 3.54-3.65 (m, 4H, CH$_2$N5,9'-H); 2.88-3.10 (m, 4H, CH$_2$NHCH$_2$); 2.70 (s, 3H, NCH$_3$); 2.00-2.10 (m, 4H, CH$_2$CH$_2$CH$_2$ N9'H; N5HCH$_2$CH$_2$CH$_2$). Preparation of derivative 7d: 5-[3-[N-(3-Aminopropyl)-N-methylamino]propylamino]-6H-[1,2,3]triazolo[4,5,1-de]-acridin-6-one×3HCl. The method of synthesis was similar to that in the case of derivative 7b: 6b and 3,3-diamino-N-methyldipropylamine were used; yield 65%.

EXAMPLE 41

Preparation of dimer IIIh (C-2060): 9-{N-5-[(6H-[1,2,3]triazolo[4,5,1-de]-acridin-6-on-5-yl)aminopropyl]-N-methylaminopropylamino}-4'-methyl-1'-nitroacridine×3HCl. The method of synthesis and purification of the product was similar to that in the case of derivative IIIa: 7d and 3b were used; the reaction temperature—100° C., the time was 1h, yield 36%, m.p. 203-205° C. Elemental analysis: $C_{34}H_{35}N_8O_3Cl_3 \times 3H_2O$. $^1$H NMR (Me$_2$SO-d$_6$+TFA) δ: 9.31 (t, 1H, N5H); 8.44 (d, J=7.8, Hz, 1H, C10); 8.33 (d, J=7.8 Hz, 1H, C7); 8.24 (d, J=9.3 Hz, 1H, C3); 8.17 (d, J=7.8 Hz, 1H, C5'); 8.10 (d, J=7.8 Hz, 1H, C2'); 7.89-7.98 (m, 2H, C6', C8); 7.82-7.87 (m, 1H, C3'); 7.54-7.63 (m, 2H, C9, C7'); 7.14 (d, J=9.3 Hz, 1H, C4); 3.41-3.75 (m, 4H, CH$_2$N5,9'-H); 2.95-3.08 (m, 4H, CH$_2$NCH$_3$CH$_2$); 2.72 (s, 3H, NCH$_3$); 2.00-2.18 (m, 4H, CH$_2$CH$_2$CH$_2$ N9'H; N5HCH$_2$CH$_2$CH$_2$).

EXAMPLE 42

Preparation of dimer IIIi (C-2061): 9-{N-5-[(6H-[1,2,3]triazolo[4,5,1-de]-acridin-6-on-5-yl)aminopropyl]-aminopropylamino}-4'-methyl-1'-nitroacridine×3HCl. The method of synthesis and purification of the product was similar to that in the case of derivative Ma: 7e and 3b were used; the reaction temperature—100° C., the time was 1.5h, yield 44%, m.p. 228-229° C. Elemental analysis: $C_{33}H_{33}N_8O_3Cl_3 \times 2H_2O$. $^1$H NMR (Me$_2$SO-d$_6$+TFA) δ: 9.33 (t, 1H, N5H); 8.60-8.66 (m, 1H, C8'); 8.45 (d, J=8.3 Hz, 1H, C10); 8.36 (d, J=8.3 Hz, 1H, C7); 8.26 (d, J=9.3 Hz, 1H, C3); 8.16 (d, J=8.8 Hz, 1H, C5'); 8.11 (d, J=7.8 Hz, 1H, C2'); 7.90-7.96 (m, 2H, C6', C8); 7.82 (d, J=7.8 Hz, 1H, C3'); 7.63 (t, J=7.8 Hz, 1H, C9); 7.54-7.58 (m, 1H, C7'); 7.15 (d, J=9.3 Hz, 1H, C4); 3.62-3.70 (m, 4H, CH$_2$N5,9'-H); 2.87-3.05 (m, 4H, CH$_2$NHCH$_2$); 1.95-2.10 (m, 4H, CH$_2$CH$_2$CH$_2$N9'H; N5HCH$_2$CH$_2$CH$_2$). Preparation of derivative 7e: 5-{3-[N-(3-Aminopropyl)-amino]propylamino}-6H-[1,2,3]triazolo[4,5,1-de]-acridin-6-one×3 HCl. The method of synthesis was similar to that in the case of derivative 7a: 6b and bis(3-aminopropyl)amine were used; yield 63%.

EXAMPLE 43

Preparation of dimer IIIj (C-2062): 9-{N-5-[(6H-[1,2,3]triazolo[4,5,1-de]-acridin-6-on-5-yl)aminopropyl]-aminopropylamino}-1'-nitroacridine×3HCl. The method of synthesis and purification of the product was similar to that in the case of derivative IIIa: 7e and 3a were used; reaction temperature—90° C., the time was 2 h, yield 36%, m.p. 213-215° C. Elemental analysis: $C_{32}H_{31}N_8O_3Cl_3 \times H_2O$. $^1$H NMR (Me$_2$SO-d$_6$+TFA) δ: 9.30 (t, 1H, N5H); 8.43 (d, J=8.3 Hz, 1H, C10); 8.38-8.42 (m, 1H, C8'); 8.34 (d, J=7.8 Hz, 1H, C7); 8.24 (d, J=9.3 Hz, 1H, C3); 8.17 (d, J=7.8 Hz, 1H, C2'); 8.07 (d, J=8.8 Hz, 1H, C5'); 7.97 (t, J=7.8 Hz, 1H, C3'); 7.90-7.96 (m, 2H, C6', C8); 7.81 (d, J=8.3 Hz, 1H, C4'); 7.62 (t, J=7.8 Hz, 1H, C9); 7.55 (t, J=7.8 Hz, 1H, C7'); 7.13 (d, J=9.3 Hz, 1H, C4); 3.60-3.73 (m, 4H, CH$_2$N5,9'-H); 2.90-3.05 (m, 4H, CH$_2$NHCH$_2$); 2.00-2.10 (m, 4H, CH$_2$CH$_2$CH$_2$ N9'H; N5HCH$_2$CH$_2$CH$_2$).

EXAMPLE 44

Cytotoxic activity tests in-vitro. A measure of the cytotoxic activity of bis-acridines are the EC$_{50}$ (concentration of studied compounds at which 50% inhibition of proliferation of tumorous is observed) of the evaluated compounds that inhibit the growth of 50% of cells in relation to a control. The cytotoxic activity of the compounds was determined using SRB, recommended by the US National Cancer Institute (USA). As the spectrum of 13 human origin neoplasms in bis-acridine screening studies, we used the following: HT 29 [CRC], HCT 116 [CRC], H 460 [lung cancer], MDA MB 231 [breast cancer], MCF-7 [breast cancer], UM UC3 [bladder cancer], PC 3 [prostate cancer], DU 145 [ prostate cancer], Panc-1 [pancreatic cancer], Mia Pa Ca 2 [pancreatic cancer], BXPC 3 [pancreatic cancer], AsPC1 [pancreatic cancer], Capan-2 [pancreatic cancer]. The EC$_{50}$ values determined for the evaluated bis-acridines are shown in Table 4. The highest sensitivity to bis-acridine activity was demonstrated by the prostate cancer DU-145 and for this reason, all 43 obtained bis-acridines were tested on it. All 43 bis-acridines exhibited cytotoxic activity against DU 145 (EC$_{50}$ below 1 μM), whereas 16 bis-acridines showed very high cytotoxic activity (EC$_{50}$ in the range 0.01-0.03 μM) in comparison to these neoplasms. The DU-145 results were substantially a basis for selecting compounds and neoplasms for screening. The next neoplasms most sensitive to the cytotoxic activity of bis-acridines was the CRC HCT-116, as well as breast cancer MBA-MB-231. In that case, an HCT-116 EC$_{50}$ in the range of 0.01-0.03 μM was shown by 12 bis-acridines out of 27 tested, and in the case of MDA-MB-231, 11 bis-acridines out of 22 tested. The cytotoxic activity of the remaining bis-acridines is significant or high (EC$_{50}$ in the range from 1 to 0.04 μM). Variable sensitivity to the cytotoxic activity of dimers of imidazoacridono-1NO$_2$-acridine is exhibited by pancreatic cancers. Panc-1, MiaPaCa-2 and Capan-2 are more sensitive, whereas for AsPC-1 and BxPC-3 this activity is at least an order of magnitude smaller. It should be stressed that al of the 43 obtained bis-acridines in tests on the 12 selected neoplasm types exhibited cytotoxic activity (EC$_{50}$<1 μM), as in the case of the prostate cancer cells DU 145.

TABLE 4

Cytotoxic activities of bis-acridines against neoplasm cells of human origin expressed as $EC_{50}$ values.

| | | | | | | | Line | | | | | | | | |
|---|---|---|---|---|---|---|---|---|---|---|---|---|---|---|---|
| No | compound | DU-145 $EC_{50}$ μM | PC-3 $EC_{50}$ μM | HT-29 $EC_{50}$ μM | H-460 $EC_{50}$ μM | HCT-116 $EC_{50}$ μM | UM-UC-3 $EC_{50}$ μM | MCF-7 $EC_{50}$ μM | MDA-MB-231 $EC_{50}$ μM | PANC-1 $EC_{50}$ μM | MiaPaCa-2 $EC_{50}$ μM | BxPC-3 $EC_{50}$ μM | AsPC-1 $EC_{50}$ μM | Capan-2 $EC_{50}$ μM |
| | | | | | ASYMMETRIC DIMERS OF ACRIDONO-1NITROACRIDINE | | | | | | | | | |
| 1 | C-1906 | 0.043 | 0.052 | 0.022 | 0.014 | 0.015 | 0.014 | 0.074 | 0.020 | 0.032 | 0.024 | | 0.135 | |
| 2 | C-1941 | 0.020 | 0.031 | 0.038 | 0.020 | 0.011 | 0.033 | 0.061 | 0.012 | 0.043 | 0.012 | | 0.210 | |
| 3 | C-1942 | 0.025 | | 0.049 | | | | | 0.039 | 0.040 | | | | |
| 4 | C-1965 | 0.243 | | 0.138 | | | | | 0.137 | 0.212 | | | | |
| 5 | C-1973 | 0.020 | 0.048 | 0.023 | 0.005 | 0.019 | 0.0095 | 0.113 | 0.028 | 0.027 | 0.016 | 0.059 | 0.079 | |
| 6 | C-2016 | 0.599 | | 0.413 | | | | | | | | | | |
| 7 | C-2017 | 0.046 | | 0.061 | 0.040 | 0.047 | | | 0.048 | | 0.067 | | | |
| 8 | C-2019 | 0.073 | | 0.200 | 0.046 | | | | | | | | | |
| 9 | C-2020 | 0.061 | | 0.233 | 0.047 | | | | | | | | | |
| 10 | C-2021 | 0.078 | | 0.129 | 0.073 | 0.088 | | | | | | | | |
| 11 | C-2022 | 0.129 | | 1.300 | 0.067 | 0.085 | 0.105 | | | 0.162 | | | | |
| 12 | C-2023 | 0.190 | | 0.123 | 0.071 | 0.120 | | | | | | | | |
| 13 | C-2024 | 0.417 | | 1.177 | 0.370 | 1.270 | | | | | | | | |
| 14 | C-2026 | 0.024 | 0.051 | 0.067 | 0.010 | 0.260 | 0.029 | 0.695 | 0.028 | 0.028 | 0.103 | | 0.066 | |
| 15 | C-2029 | 0.044 | | 0.230 | 0.055 | 0.074 | 0.054 | | | 0.110 | | | | |
| 16 | C-2030 | 0.041 | 0.362 | | 0.040 | 0.083 | 0.063 | | | 0.130 | 0.108 | | | |
| 17 | C-2031 | 0.011 | 0.026 | | 0.009 | 0.020 | 0.017 | 0.077 | 0.028 | 0.056 | 0.028 | | 0.078 | |
| 18 | C-2032 | 1.692 | | | | 0.850 | 0.730 | | | 1.310 | | | | |
| 19 | C-2033 | 0.010 | 0.032 | | | 0.019 | 0.015 | 0.072 | 0.032 | 0.038 | 0.048 | | | |
| 20 | C-2038 | 0.184 | | | | | | 0.228 | | 0.377 | 0.280 | | | |
| 21 | C-2039 | 0.088 | | | | | | | | 0.142 | 0.110 | | | |
| 22 | C-2040 | 0.055 | | | | | | | | 0.060 | 0.046 | | | |
| | | | | | ASYMMETRIC DIMERS OF IMIDAZOACRIDONO-1NITROACRIDINE | | | | | | | | | |
| 1 | C-2025 | 0.067 | 0.130 | 0.237 | 0.074 | 0.051 | 0.035 | 0.244 | 0.017 | 0.042 | 0.038 | 0.354 | 0.343 | 0.068 |
| 2 | C-2027 | 0.020 | 0.035 | 0.081 | 0.017 | 0.020 | 0.018 | 0.062 | 0.019 | 0.024 | 0.021 | 0.164 | 0.191 | 0.043 |
| 3 | C-2028 | 0.023 | 0.028 | 0.037 | 0.015 | 0.017 | 0.010 | 0.053 | 0.017 | 0.024 | 0.079 | 0.074 | 0.061 | 0.011 |
| 4 | C-2037 | 0.040 | | | | 0.102 | | 0.082 | 0.027 | 0.037 | 0.064 | 0.138 | 0.086 | 0.044 |
| 5 | C-2041 | 0.022 | | | | 0.025 | | 0.082 | 0.021 | 0.024 | 0.039 | 0.054 | 0.069 | 0.032 |
| 6 | C-2042 | 0.021 | | | | 0.018 | | 0.049 | 0.018 | 0.055 | 0.047 | 0.081 | 0.082 | 0.029 |
| 7 | C-2045 | 0.059 | | | | 0.040 | | | 0.052 | 0.216 | 0.059 | 0.169 | 0.152 | 0.052 |
| 8 | C-2049 | 0.021 | | | | 0.028 | | | 0.038 | 0.040 | 0.036 | 0.075 | 0.122 | 0.027 |
| 9 | C-2050 | 0.062 | | | | 0.045 | | | | 0.065 | 0.058 | 0.351 | 0.240 | |
| 10 | C-2051 | 0.024 | | | | 0.027 | | | | 0.039 | 0.018 | 0.152 | 0.151 | |
| 11 | C-2053 | 0.065 | | | | 0.065 | | | | 0.098 | 0.087 | 0.224 | 0.176 | |
| | | | | | ASYMMETRIC DIMERS OF TRIAZOLOACRIDONO-1NITROACRIDINE | | | | | | | | | |
| 1 | C-2047 | 0.017 | | | | | | 0.029 | 0.036 | 0.017 | | | 0.137 | |
| 2 | C-2048 | 0.022 | | | 0.022 | | | 0.152 | 0.138 | 0.041 | 0.120 | 0.103 | | 0.033 |
| 3 | C-2052 | 0.028 | | | | | | | | 0.074 | 0.066 | 0.155 | 0.220 | |
| 4 | C-2056 | 0.038 | | | | | | | | 0.118 | | | | |
| 5 | C-2057 | 0.034 | | | | | | | | 0.066 | | | | |
| 6 | C-2058 | 0.042 | | | | | | | | 0.081 | | | | |
| 7 | C-2060 | 0.15 | | | | | | | | 0.185 | | | | |
| 8 | C-2061 | 0.039 | | | | | | | | 0126 | | | | |
| 9 | C-2062 | 0.038 | | | | | | | | 0.058 | | | | |
| 10 | C-2063 | 0.0046 | | | | | | | | 0.024 | | | | |

EXAMPLE 45

Anti-Neoplasmic Activity Against Xenografts of Neoplasms of Human Origin on Mice Lacking a Thymus Currently, the most significant results in tests of anti-neoplasmic activity are obtained using xenografts, of human origin neoplasm, especially those which cells exhibit high sensitivity in vitro. For this, we selected 26 bis-acridines, mainly on the basis of the cytotoxic activity. We performed 34 series of experiments evaluating the anti-neoplasmic activity on xenografts in hairless mice against eleven neoplasms of human origin from the determination of the cytotoxic activity of bis-acridines (table 4). The tumours were injected subcutaneously to hairless mice of 5-weeks, female Crl:Nu-Foxnlnu, at a rate of $5\times10^6$ cells per mouse. After attaining a tumour of about 100 mm$^3$ or 200 mm$^3$ in depending on the neoplasm and its take this was 8 or even 30 days, and began therapy. On the day therapy was initiated, we randomised the animals and divided them into groups. Test groups were from 6 to 8 animals, and controls had from 8 to 14 animals. Each compound was tested at three differentiated doses.

The preparations were administered intravenously (i.v.) twice weekly for 4 weeks (thrice weekly for rapidly growing neoplasms). In several series, we used intraperitoneally (i.p.) administration in the same scheme. (I.p.) administration resulted in a much higher toxicity than (i.v.), and thus further on we used only (i.v.). The therapeutic efficacy of the tested formulations was evaluated by measuring tumour size (length and width measurements of the tumour on the basis of the calculated tumour volume). Tumours were measured twice weekly for a period of about 30 days for fast-growing neoplasms, as well as about 60 days for the slow-growing neoplasms. The tumour volume in the treated groups compared with the control group. On this basis, inhibition of tumour growth was calculated using the following formula: Tumour growth inhibition TGI [%]=100−($\Delta$VT/$\Delta$VC×100) Where $\Delta$VT—is mean the tumour volume in animals in the group treated at the given day of treatment, minus the mean tumour volume in animals at the date of commencement of therapy. $\Delta$VC is mean tumour volume in animals in the control group on a given day of treatment minus the average tumour volume of animals on the date of commencement of therapy. The results of the tests of anti-neoplasmic activity conducted in xenografts of human-origin neoplasms in mice are shown in Table 5.

The resulting table shows the maximum percent inhibition of growth neoplasms dose specified as the optimum as well as a day in which the result in obtained. The result above was accepted only in the case that the dose administered in all animals or more than half of the animals that survived to the end of the experiment. In addition, the evaluation was the day that the administration of the preparation was already completed: for the fast-growing neoplasms (eg. HCT116) this was in the days from 15 to 26, while for slow-growing neoplasms (eg. Panc 1) on a day from 34 to 60. These results inhibit the growth of neoplasms shown in percentage growth inhibition around the test neoplasms in the series (3 different doses). In addition, the maximum inhibition of neoplasms could be identified in the day, in which there were no factors that could change the value TGI value.

Such factors may include: a significant decrease in body weight, the appearance of observable toxaemia, excessive rate of tumour growth: tumours in excess of 2000 mm$^3$ and all animals alive on that day.

TABLE 5

Determination of the anti-neoplasmic activity of bis-acridines against xenografted neoplasms of human origin in hairless mice (with divisions into chemical groups)

A. ASYMMETRIC DIMERS OF ACRIDONO-1-NITROACRIDINE

| Preparation | SERIES | | ROUTE | OPTIMAL SINGLE DOSE [mg/kg] | OPTIMAL TOTL DOSE [mg/kg] | DAY OF EVALUATION | TGI [%] [100 − ($\Delta_{VT}/\Delta_{VC}$ × 100] |
|---|---|---|---|---|---|---|---|
| | Serial no. | Neoplasm | | | | | |
| C-1906 | 1 | DU 145 | i.p. | 2 | 6 | 35 | 60* |
| | 15 | PC 3 | i.p. | 2 | 12 | 39 | 52 |
| | 9 | HCT 116 | i.v. | 1 | 5 | 16 | 32* |
| C-1941 | 2 | DU 145 | i.p. | 4 | 24 | 35 | 52 |
| | 12 | Mia Pa Ca 2 | i.p. | 4 | 32 | 26 | 30 |
| | 3 | H T29 | i.v. | 3 | 24 | 20 | 26 |
| | 3 | H T29 | i.v. | 4 | 24 | 20 | 35 |
| | 4 | H 460 | i.v. | 15 | 30 | 14 | 24 |
| C-1965 | 1 | DU 145 | i.p. | 8 | 40 | 35 | 61* |
| C-1973 | 13 | DU 145 | i.v. | 4 | 32 | 63 | 90 |
| | 18 | DU 145 | i.v. | 1 | 8 | 33 | 51 |
| | 31 | PANC 1 | i.v. | 2 | 16 | 37 | 75 |
| | 19 | MDA MB 231 | i.v. | 1 | 8 | 50 | 30 |
| | 16 | H 460 | i.v. | 2 | 10 | 21 | 42 |
| | 11 | UM UC 3 | i.v. | 2 | 14 | 23 | 46 |
| C-2017 | 2 | DU 145 | i.p. | 8 | 48 | 35 | 25 |
| | 5 | H 460 | i.p. | 5 | 30 | 14 | 6 |
| | 31 | PANC 1 | i.v. | 15 | 120 | 51 | 75 |
| C-2022 | 5 | H 460 | i.p. | 10 | 60 | 14 | 25 |
| C-2026 | 16 | H 460 | i.v. | 1 | 5 | 15 | 14 |
| C-2029 | 8 | HCT 116 | i.p. | 20 | 100 | 23 | 52 |
| C-2030 | 6 | H 460 | i.v. | 10 | 60 | 17 | 24* |
| C-2031 | 13 | DU 145 | i.v. | 4 | 32 | 35 | 77 |
| | 18 | DU 145 | i.p. | 1 | 8 | 64 | 81 |
| | 15 | PC 3 | i.v. | 1 | 8 | 39 | 30 |
| | 14 | PANC 1 | i.v. | 1 | 10 | 37 | 27 |
| | 10 | PANC 1 | i.v. | 3 | 30 | 45 | 72 |
| | 9 | HCT 116 | i.v. | 3 | 24 | 30 | 34 |
| | 8 | HCT 116 | i.v. | 6 | 18 | 14 | 52* |
| | 6 | H 460 | i.v. | 8 | 48 | 23 | 60 |
| C-2033 | 8 | HCT 116 | i.p. | 3 | 21 | 23 | 37 |

*At least half of the animals did not survive 60 days in the case of the slowly growing neoplasms (Panc 1. DU 145) and 30 days in the case of t rapidly growing ones,

B. ASYMMETRIC DIMERS OF TRIAZOLOACRIDONO-1-NITROACRIDINE

| Preparation | SERIES | | ROUTE | OPTIMAL SINGLE DOSE [mg/kg] | OPTIMAL TOTL DOSE [mg/kg] | DAY OF EVALUATION | TGI [%] [100 − ($\Delta_{VT}/\Delta_{VC}$ × 100] |
|---|---|---|---|---|---|---|---|
| | SERIES NO. | TUMOUR | | | | | |
| C-2047 | | | | Not tested | | | |
| C-2048 | 30 | PANC 1 | i.v. | 4 | 24 | 52 | 86 |
| C-2052 | 30 | PANC 1 | i.v. | 1 | 8 | 52 | 39 |

TABLE 5-continued

Determination of the anti-neoplasmic activity of bis-acridines against xenografted
neoplasms of human origin in hairless mice (with divisions into chemical groups)

C. ASYMMETRIC DIMERS OF IMIDAZOACRIDONO-1-NITROAKRYDYN

| Preparation | SERIE SERIES NO. | TUMOUR | ROUTE | OPTIMAL SINGLE DOSE [mg/kg] | OPTIMAL TOTL DOSE [mg/kg] | DAY OF EVALUATION | TGI [%] [100 − ($\Delta_{VT}/\Delta_{VC}$ × 100] |
|---|---|---|---|---|---|---|---|
| C-2025 | 20 | PANC 1 | i.v. | 20 | 160 | 26 | 61* |
|  | 19 | MDA MB 231 | i.v. | 5 | 40 | 39 | 12 |
|  | 7 | HCT 116 | i.v. | 20 | 120 | 15 | 4 |
| C-2026 | 16 | H 460 | i.v. | 4 | 16 | 14 | 35* |
| C-2027 | 10 | PANC 1 | i.v. | 2 | 10 | 45 | 83 |
|  | 30 | PANC 1 | i.v. | 1 | 8 | 32 | 51* |
|  | 14 | PANC 1 | i.v. | 1 | 10 | 45 | 23 |
|  | 12 | Mia Pa Ca 2 | i.v. | 2 | 16 | 26 | 29 |
|  | 11 | UM UC 3 | i.v. | 4 | 28 | 23 | 47 |
|  | 7 | HCT 116 | i.v. | 2.5 | 15 | 15 | 15 |
| C-2028 | 10 | PANC 1 | i.v. | 1 | 10 | 31 | 71 |
|  | 14 | PANC 1 | i.v. | 4 | 36 | 45 | 90 |
|  | 32 | PANC 1 | i.v | 2 | 16 | 40 | 82 |
|  | 29 | PANC 1 | i.v. | 4 | 20 | 36 | 59 |
|  | 21 | BXPC-3 | i.v. | 6 | 30 | 37 | 64 |
|  | 33 | BXPC 3 | i.v. | 4 | 32 | 36 | 43 |
|  | 12 | Mia Pa Ca 2 | i.v. | 6 | 42 | 36 | 52 |
|  | 28 | Mia Pa Ca 2 | i.v. | 2 | 8 | 11 | 68* |
|  | 23 | AsPC 1 | i.v. | 6 | 48 | 46 | 35 |
|  | 11 | UM UC 3 | i.v. | 6 | 42 | 23 | 54 |
|  | 13 | DU 145 | i.v. | 4 | 32 | 40 | 46 |
|  | 12 | PC 3 | i.p. | 1 | 8 | 39 | 30 |
|  | 19 | MDA MB 231 | i.v. | 2 | 16 | 25 | 44 |
|  | 16 | H 460 | i.v. | 1 | 5 | 28 | 31 |
|  | 7 | HCT 116 | i.v. | 4 | 24 | 15 | 34 |
| C-2037 | 17 | PANC 1 | i.v. | 4 | 16 | 39 | 60 |
| C-2041 | 17 | PANC 1 | i.v. | 2 | 16 | 60 | 76 |
|  | 27 | PANC 1 | i.v. | 2 | 16 | 33 | 83 |
|  | 32 | PANC 1 | i.v. | 1 | 16 | 33 | 82 |
|  | 21 | BXPC 3 | i.v. | 2 | 16 | 44 | 81 |
|  | 33 | BXPC 3 | i.v. | 2 | 16 | 32 | 48 |
|  | 23 | AsPC 1 | i.p. | 2 | 16 | 39 | 29 |
|  | 28 | Mia Pa Ca 2 | i.v. | 6 | 12 | 15 | 38* |
|  | 18 | DU 145 | i.v. | 2 | 16 | 33 | 61 |
|  | 34 | MDA MB 231 | i.v. | 4 | 32 | 32 | 53 |
| C-2042 | 17 | PANC 1 | i.v. | 4 | 20 | 39 | 33* |
| C-2045 | 24 | PANC 1 | i.v. | 2 | 16 | 44 | 82 |
|  | 20 | PANC 1 | i.v. | 10 | 40 | 32 | 67 |
|  | 29 | PANC 1 | i.v. | 5 | 25 | 36 | 25 |
|  | 26 | PANC 1 | i.v. | 10 | 80 | 56 | 64 |
|  | 25 | BXPC 3 | i.p. | 10 | 80 | 32 | 77 |
|  | 28 | Mia Pa Ca 2 | i.v. | 5 | 28 | 33 | 55 |
| C-2049 | 27 | PANC 1 | i.v | 2 | 16 | 47 | 80 |
|  | 20 | PANC 1 | i.v. | 6 | 48 | 32 | 63 |
|  | 21 | BXPC 3 | i.v. | 6 | 40 | 34 | 63 |
|  | 23 | AsPC 1 | i.v. | 6 | 48 | 36 | 32* |
| C-2050 | 24 | PANC 1 | i.v. | 20 | 160 | 50 | 64 |
|  | 26 | PANC 1 | i.v. | 30 | 160 | 40 | 64 |
|  | 25 | BXPC 3 | i.v. | 20 | 160 | 29 | 40 |
| C-2051 | 27 | PANC 1 | i.v. | 2 | 16 | 40 | 68* |
| C-2053 | 24 | PANC 1 | i.v. | 15 | 120 | 37 | 64 |
|  | 26 | PANC 1 | i.v. | 20 | 160 | 56 | 69 |
|  | 25 | BXPC 3 | i.v. | 20 | 160 | 36 | 84 |
|  | 33 | BXPC 3 | i.v. | 20 | 160 | 32 | 47* |
|  | 34 | MDA MB 231 | i.v. | 15 | 120 | 32 | 62 |

*At least half of the animals did not survive to 60 days in the case of slowly growing neoplasms (Panc 1, DU 145) and 30 days for fast growing ones (HCT 116, H460)

As the evaluation criterion we accepted the following scale of inhibition: TGI<60% threshold activity, TGI≥60% as significant activity, TGI≥80% as high activity, TGI≥90% as very high activity.

These tests were performed for 26 example bis-acridines on 11 neoplasms of human origin. A neoplasm particularly sensitive to the tested bis-acridines is prostate cancer DU 145 against which, a significant activity (neoplasm growth inhibition TGI>60-80%) was exhibited by 6 compounds, including two dimers of imidazoacridono-1-nitroacridine. Unfortunately these do not inhibit the rapidly growing prostate cancer PC-3. The largest group of neoplasms of human origin sensitive to bis-acridine activity, particularly of the imidazoacridono-1-nitroacridine type, were pancreatic cancers. of 11 obtained imidazoacridono-1-nitroacridines 9 showed a significant or high activity against pancreatic cancers (TGI>60-80%). The highest activity against pancreatic cancers was shown by bis-acridine C-2028 against PANC-1 cancer, in three consecutive experimental runs we obtained a TGI of 71%, 90% and 82%. Significant activity was also shown against BXPC-3 (TGI 64%) as well as threshold activity (TGI<50%) against two further pancreatic cancers (MiaPa Ca2 and ASP-1). A high anti-neoplasmic activity against PANC-1 and BXPC-3 (TGI 65% to 81%) was shown by three further compounds from the same group of imidazoacridono-1-nitroacridines (C-2041, C-2045, C-2053). In the case of bis-acridines exhibiting a high anti-neoplasmic activity, we repeated the determinations. For example, the full results of the determination of anti-neoplasmic activity of bis-acridine C-2028 from series 14 against Panc-1 is shown in graphic form in FIG. 1

The discernment of a compound with strong anti-neoplasmic activity against pancreatic cancers of human origin is the most significant result of this research. Pancreatic cancers are the most lethal solid tumours, essentially untreatable, and insensitive to anti-neoplasmic drugs. In developed countries, they occupy 4th place among neoplasms as a cause of death. It should be also stressed that the activity of bis-acridines is highly effective against prostate cancer DU 145, whose growth was inhibited to a significant degree (TGI>60%-90%) by six compounds. Also, one of the bis-acridines with a triazoloacridone group, C-2052, exhibited a high level of activity against Panc-1 pancreatic cancer.

The invention claimed is:

1. A compound defined by the formula:

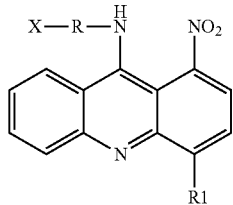

wherein:

R denotes a group selected from among: (CH$_2$)$_n$NH (CH$_2$)$_n$, (CH$_2$)$_n$NCH$_3$(CH$_2$)$_n$, (CH$_2$)$_n$piperazinyl(1,4) (CH$_2$)$_n$ or (CH$_2$)$_n$NH(CH$_2$)$_n$NH(CH$_2$)$_n$, among which n is an integer from 2 to 4, R1 denotes H or CH$_3$, X denotes the group selected from among:

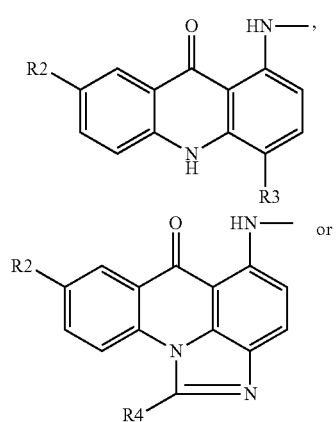

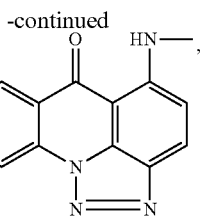

wherein R2 denotes H, OH or OCH$_3$, R3 denotes H, NO$_2$ or CH$_3$, a R4 denotes H or CH$_3$, or a pharmaceutically admissible salt thereof, in particular hydrochloride or methanesulphonate.

2. A compound according to claim 1, characterised in that X denotes the group:

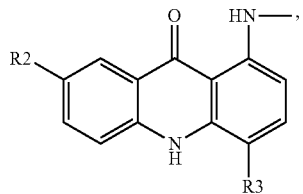

wherein R2 and R3 as defined in claim 1 and wherein X is selected from among the following compounds:
9-{N-[(7-hydroxy-4-nitro-9(10H)acridono-1-yl)aminopropyl]-N-methylaminopropylamino}-1'-nitroacridone×2HCl,
1-[3-(7-hydroxy-4-nitro-9(10H)-acridono-1-yl)aminopropyl]-4-3'-(1'-nitroacridin-1-yl)-aminopropyl]piperazine×3HCl,
9-{N-[(4-methyl-9(10H)-acridono-1-yl)aminoethyl]ethylamino}-1'-nitroacridine×3HCl,
1-[3-(4-methyl-9(10H)-acridono-1-yl)aminopropyl]-4-3'-[(1'-nitroacridin-1-yl)-aminoprop yl]piperazine×4HCl,
9-[N-(4-methyl-9(10H)acridono-1-yl)-aminoethylamino-ethylamino]-1'-nitroacridine×4HCl,
9-{N-[(4-methyl-9(10H)-acridono-1-yl)aminoethyl]ethylamino}-4'-methyl-1'-nitroacridine×2CH$_3$SO$_2$OH,
1-[3-(4-methyl-9(10H)-acridono-1-yl)aminopropyl]-4-[3'-(4'-methyl-1'-nitroacridin-1-yl)-aminopropyl]piperazine×3 CH$_3$SO$_2$OH,
9-{N-[(7-hydroxy-4-nitro-9(10H)acridono-1-yl)aminopropyl]-N-methylaminopropylamino}-4'-methyl-1'-nitroacridine×2HCl,
1-[3-(7-hydroxy-4-nitro-9(10H)-acridono-1-yl)aminopropyl]-4-[3'-(4'-methyl-1'-nitro-acridin-1-yl)-aminopropyl]piperazine×3HCl,
9-{N-[(7-hydroxy-4-nitro-9(10H)acridono-1-yl)aminopropyl]-aminopropylamino}-4'-methyl-1'-nitroacridine×2HCl,
9-{N-[(4-methyl-9(10H)-acridono-1-yl)aminopropyl]propylamino}-4'-methyl-1'-nitroacridine×3HCl,
9-{N-[(4-methyl-9(10H)-acridono-1-yl)aminopropyl]-N-methylaminopropylamino}-4'-methyl-1'-nitroacridine×3HCl,
9-[N-(4-methyl-9(10H)acridono-1-yl)-aminoethylamino-ethylamino-ethylamino]-4'-methyl-1'-nitroacridine×4HCl,
9-{N-[(4-nitro-9(10H)acridono-1-yl)aminopropyl]-N-methylaminopropylamino}-1'-nitroacridine×2HCl,
9-{N-[(4-nitro-9(10H)acridono-1-yl)aminopropyl]-N-methylaminopropylamino}-4'-methyl-1'-nitroacridine×2HCl, 1-[3-(4-nitro-9(10H)-acridono-1-yl)aminopropyl]-4-[3'-(4'-methyl-1'-nitroacridin-1-yl)-aminopropyl]piperazine×3HCl, 1-[3-(4-nitro-9(10H)-acridono-1-yl)aminopropyl]-4-[3'-(1'-nitroacridin-1-yl)-aminopropyl]piperazine×3HCl, 9-[N-(4-nitro-9(10H)acridono-1-yl)-aminoethylamino-ethylamino-ethylamino]-4'-methyl-1'-nitroacridine×3HCl, 9-[N-(4-nitro-9(10H)acridono-1-yl)-aminoethylamino-ethylamino-ethylamino]-1'-nitroacridine×3HCl, 9-{N-[(4-methyl-9(10H)-acridono-1-yl)aminopropyl]propylamino}-1'-nitroacridine×3HCl, 9-[N-(4-nitro-9(10H)acridono-1-yl)-aminopropylamino-ethylamino-propylamino]-4'-methyl-1'-nitroacridine×3HCl, and 9-[N-(4-nitro-9(10H)acridono-1-yl)-aminopropylamino-ethylamino-propylamino]-1'-nitroacridine×3HCl.

3. A compound according to claim 1, characterised in that X denotes the group:

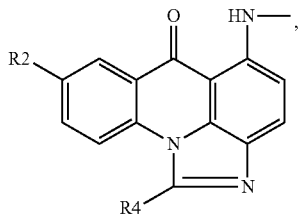

wherein R2 and R4 as defined in claim 1 and wherein X is selected from among the following compounds:

1-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-imidazo[4,5,1-de]-acridin-6-on-5-yl)aminopropyl]-4-[3'-(1'-nitroacridin-1-yl)-aminopropyl]piperazine×3HCl, 9-{N-[(imidazo[4,5,1-de]-acridin-6-on-5-yl)aminopropyl]-N-methylaminopropylamino}-1'-nitroacridine×1.5HCl, 9-[N-(imidazo[4,5,1-de]-acridin-6-on)-aminoethylamino-ethylamino-ethylamino]-4'-methyl-1'-nitroacridine×4HCl, 1-[3-(imidazo[4,5,1-de]-acridin-6-on-5-yl)aminopropyl]-4-[3'-(1'-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-1'-nitroacridine×3HCl, 9-{N-[(8-hydroxyimidazo[4,5,1-de]-acridin-6-on-5-yl)aminopropyl]-N-methylaminopropyl amino}-4'-methyl-1'-nitroacridine×3HCl, 1-[3-(8-methoxy-imidazo[4,5,1-de]-acridin-6-on-5-yl)aminopropyl]-4-[3'-(1'-nitroacridin-1-yl)-aminopropyl]piperazine×4HCl, 1-[3-(imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl, and 9-{N-[(imidazo[4,5,1-de]-acridin-6-on-5-yl)aminopropyl]-N-methylaminopropylamino}-4'-methyl-1'-nitroacridine×3HCl.

4. A compound according to claim 1, characterised in that X denotes the group:

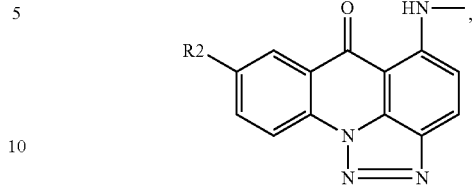

wherein R2 is defined in claim 1 and wherein X is selected from among the following compounds:

1-[3-(8-hydroxy-6H-[1,2,3]triazolo[4,5,1-de]-acridin-6-on-5-yl)aminopropyl]-4-[3'-(1'-nitroacridin-1-yl)-aminopropyl]piperazine×4HCl, 1-[3-(6H-[1,2,3]triazolo[4,5,1-de]-acridin-6-on-5-yl)aminopropyl]-4-[3'-(1'-nitroacridin-1-yl)-aminopropyl]piperazine×4HCl, 9-{N-[(8-hydroxy-6H-[1,2,3]triazolo[4,5,1-de]-acridin-6-on-5-yl)aminopropyl]-N-methylaminopropylamino}-1'-nitroacridine×2CH₃SO₂OH, 9-{N-5-[(8-hydroxy-6H-[1,2,3]triazolo[4,5,1-de]-acridin-6-on-5-yl)aminopropyl]-N-methyl aminopropylamino}-4'-methyl-1'-nitroacridine×3 HCl, 1-[3-(8-hydroxy-6H-[1,2,3]triazolo[4,5,1-de]-acridin-6-on-5-yl)aminopropyl]-4-[3'-(4'-methyl-1'-nitroacridin-1-yl)- aminopropyl]piperazine×4HCl, 1-[3-(6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl, 9-{N-5-[(6H-[1,2,3]triazolo[4,5,1-de]-acridin-6-on-5-yl)aminopropyl]-N-methylaminopropylamino}-1'-nitroacridine×3HCl, 9-{N-5-[(6H-[1,2,3]triazolo[4,5,1-de]-acridin-6-on-5-yl)aminopropyl]-N-methylaminopropylamino}-4'-methyl-1'-nitroacridine×3HCl, 9-{N-5-[(6H-[1,2,3]triazolo[4,5,1-de]-acridin-6-on-5-yl)aminopropyl]-aminopropylamino}-4'-methyl-1'-nitroacridine×3HCl, and 9-{N-5-[(6H-[1,2,3]triazolo[4,5,1-de]-acridin-6-on-5-yl)aminopropyl]-aminopropylamino}-1'-nitroacridine×3HCl.

5. A compound according to claim 1, further comprising a pharmaceutical carrier.

6. A method for treating an individual having neoplasms comprising the steps of: preparing a compound defined by the formula:

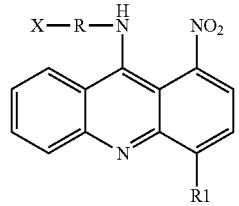

wherein:
R denotes a group selected from among: $(CH_2)_nNH(CH_2)_n$, $(CH_2)_nNCH_3(CH_2)_n$, $(CH_2)_n$piperazinyl(1,4)$(CH_2)_n$ or $(CH_2)_nNH(CH_2)_nNH(CH_2)_n$, among which n is an integer from 2 to 4,
R1 denotes H or $CH_3$, X denotes the group selected from among:

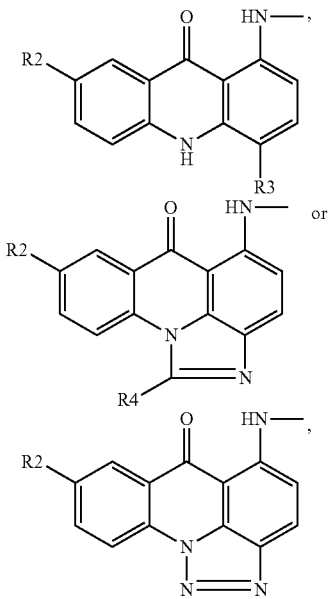

wherein R2 denotes H, OH or OCH$_3$, R3 denotes H, NO$_2$ or CH$_3$, a R4 denotes H or CH$_3$, or a pharmaceutically admissible salt thereof, hydrochloride or methanesulphonate, wherein said neoplasms are cancers of the colon, lung, breast, bladder, prostate and/or pancreas, and administering said compound to said individual.

7. A method according to claim 6, wherein said neoplasm is a pancreatic tumor, and said compound is selected from among the following compounds:
- 1-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl,
- 1-[3-(8-hydroxy-imidazo[4,5,1-de]-acridin-6-on-5-yl)aminopropyl]-4-[3'-(1'-nitroacridin-1-yl)-aminopropyl]piperazine×3HCl,
- 9-{N-[(imidazo[4,5,1-de]-acridin-6-on-5-yl)aminopropyl]-N-methylaminopropylamino}-1'-nitroacridine×1.5HCl,
- 9-[N-(imidazo[4,5,1-de]-acridin-6-on)-aminoethylaminoethylamino-ethylamino]-4'-methyl-1'-nitroacridine×4HCl,
- 1-[3-(imidazo[4,5,1-de]-acridin-6-on-5-yl)aminopropyl]-4-[3'-(1'-nitroacridin-1-yl)-aminopropyl]piperazine×4HCl,
- 9-{N-[(8-hydroxyimidazo[4, 5,1-de]-acridin-6-on-5-yl)aminopropyl]-N-methylaminopropylamino}-1'-nitroacridine×3HCl,
- 9-{N-[(8-hydroxyimidazo[4, 5,1-de]-acridin-6-on-5-yl)aminopropyl]-N-methylaminopropylamino}-4'-methyl-1'-nitroacridine×3HCl,
- 1-[3-(8-methoxy-imidazo[4,5,1-de]-acridin-6-on-5-yl)aminopropyl]-4-[3'-(1'-nitroacridin-1-yl)-aminopropyl]piperazine×4HCl,
- 1-[3-(imidazo[4,5,1-de]-acridin-6-on-5-yl)aminopropyl]-4-[3'-(4'-methyl-1'-nitroacridin-1-yl)-aminopropyl]piperazine×4HCl,
- 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl,
- 9-{N-[(imidazo[4,5,1-de]-acridin-6-on-5-yl)aminopropyl]-N-methylaminopropylamino}-4'-methyl-1'-nitroacridine×3HCl,
- 1-[3-(imidazo[4,5,1-de]-acridin-6-on-5-yl)aminopropyl]-4-[3'-(1'-nitroacridin-1-yl)-aminopropyl]piperazine×4HCl,
- 9-{N-[(8-hydroxyimidazo[4, 5,1-de]-acridin-6-on-5-yl)aminopropyl]-N-methylaminopropylamino}-4'-methyl-1'-nitroacridine×3HCl,
- 9-{N-[(imidazo[4,5,1-de]-acridin-6-on-5-yl)aminopropyl]-N-methylaminopropylamino}-4'-methyl-1'-nitroacridine×3HCl,
- 9-{N-[(imidazo[4,5,1-de]-acridin-6-on-5-yl)aminopropyl]-N-methylaminopropylamino}-1'-nitroacridine×1.5HCl, and
- 9-{N-[(imidazo[4,5,1-de]-acridin-6-on-5-yl)aminopropyl]-N-methylaminopropylamino}-1'-nitroacridine×1.5HCl.

* * * * *

UNITED STATES PATENT AND TRADEMARK OFFICE
CERTIFICATE OF CORRECTION

| | | |
|---|---|---|
| PATENT NO. | : 10,202,349 B2 | Page 1 of 3 |
| APPLICATION NO. | : 15/559812 | |
| DATED | : February 12, 2019 | |
| INVENTOR(S) | : Jerzy Kazimierz Konopa et al. | |

It is certified that error appears in the above-identified patent and that said Letters Patent is hereby corrected as shown below:

In the Specification

At the first line in Column 32, "in" is replaced with "is"

At Columns 34-35, the title of Section C of Table 5 is corrected as follows:
C. ASYMMETRIC DIMERS OF IMIDAZOACRIDONO-1-NITROACRIDINE In the Claims Column 37, Lines 18-67, Claim 3, should read, (approx.):
3. A compound according to Claim 1, characterised in that X denotes the group:

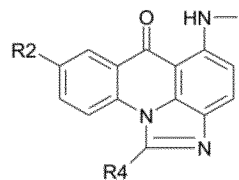

wherein R2 and R4 as defined in claim 1 and wherein X is selected from among the following compounds:
1-[3-(8-hydroxy-imidazo[4,5,1-de]-acridin-6-on-5-yl)aminopropyl]-4-[3′-(4′-methyl-1′-nitroacridin-1-yl)-aminopropyl]piperazine×4HCl, 1-[3-(8-hydroxy-imidazo[4,5,1-de]-acridin-6-on-5-yl)aminopropyl]-4-[3′-(1′-nitroacridin-1-yl)-aminopropyl]piperazine×3HCl, 9-{N-[(imidazo[4,5,1-de]-acridin-6-on-5-yl)aminopropyl]-N-methylaminopropylamino}-1′-nitroacridine×1.5HCl, 9-[N-(imidazo[4,5,1-de]-acridin-6-on)-aminoethylaminoethylamino-ethylamino]-4′-methyl-1′-nitroacridine×4HCl, 1-[3-(imidazo[4,5,1-de]-acridin-6-on-5-yl)aminopropyl]-4-[3′-(1′-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-1′-nitroacridine×3HCl, 9-{N-[(8-hydroxyimidazo[4,5,1-de]-acridin-6-on-5-yl)aminopropyl]-N-methylaminopropylamino}-4′-methyl-1′-nitroacridine×3HCl, 1-[3-(8-methoxy-imidazo[4,5,1-de]-acridin-6-on-5-yl)aminopropyl]-4-[3′-(1′-nitroacridin-1-yl)-aminopropyl]piperazine×4HCl, 1-[3-(imidazo[4,5,1-de]-acridin-6-on-5-

Signed and Sealed this
Third Day of September, 2019

Andrei Iancu
*Director of the United States Patent and Trademark Office* yl)aminopropyl]-4-[3'-(4'-methyl-1'-nitroacridin-1-yl)-aminopropyl]piperazine×4HCl, 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl, and 9-{N-[( imidazo[4,5,1-de]-acridin-6-on-5-yl)aminopropyl]-N-methylaminopropylamino}-4'-methyl-1'-nitroacridine×3HCl.

Column 38, Lines 1-45, Claim 4, should read, (approx.):
4. A compound according to Claim 1, characterised in that X denotes the group:

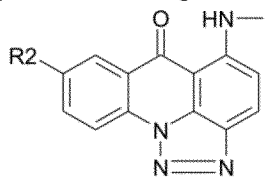

wherein R2 is defined in claim 1 and wherein X is selected from among the following compounds:
1-[3-(8-hydroxy-6H-[1,2,3]triazolo[4,5,1-de]-acridin-6-on-5-yl)aminopropyl]-4-[3'-(1'-nitroacridin-1-yl)-aminopropyl]piperazine×4HCl, 1-[3-(6H-[1,2,3]triazolo[4,5,1-de]-acridin-6-on-5-yl)aminopropyl]-4-[3'-(1'-nitroacridin-1-yl)-aminopropyl]piperazine×4HCl, 9-{N-[(8-hydroxy-6H-[1,2,3]triazolo[4,5,1-de]-acridin-6-on-5-yl)aminopropyl]-N-methylaminopropylamino}-1'-nitroacridine×2CH3SO2OH, 9-{N-5-[(8-hydroxy-6H-[1,2,3]triazolo[4,5,1-de]-acridin-6-on-5-yl)aminopropyl]-N-methylaminopropylamino}-4'-methyl-1'-nitroacridine×3HCl, 1-[3-(8-hydroxy-6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl, 1-[3-(6H-[1,2,3]triazolo[4,5,1-de]-acridin-6-on-5-yl)aminopropyl]-4-[3'-(4'-methyl-1'-nitroacridin-1-yl)-aminopropyl]piperazine×4HCl, 9-{N-5-[(6H-[1,2,3]triazolo[4,5,1-de]-acridin-6-on-5-yl)aminopropyl]-N-methylaminopropylamino}-1'-nitroacridine×3HCl, 9-{N-5-[(6H-[1,2,3]triazolo[4,5,1-de]-acridin-6-on-5-yl)aminopropyl]-N-methylaminopropylamino}-4'-methyl-1'-nitroacridine×3HCl, 9-{N-5-[(6H-[1,2,3]triazolo[4,5,1-de]-acridin-6-on-5-yl)aminopropyl]-aminopropylamino}-4'-methyl-1'-nitroacridine×3HCl, and 9-{N-5-[(6H-[1,2,3]triazolo[4,5,1-de]-acridin-6-on-5-yl)aminopropyl]-aminopropylamino}-1'-nitroacridine×3HCl.

Column 39, Line 34-Column 40, Line 42, Claim 7, should read, (approx.):
7. A method according to claim 6, wherein said neoplasm is a pancreatic tumor, and said compound is selected from among the following compounds:
1-[3-(8-hydroxy-imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-imidazo[4,5,1-de]-acridin-6-on-5-yl)aminopropyl]-4-[3'-(1'-nitroacridin-1-yl)-aminopropyl]piperazine×3HCl, 9-{N-[(imidazo[4,5,1-de]-acridin-6-on-5-yl)aminopropyl]-N-methylaminopropylamino}-1'-nitroacridine×1.5HCl, 9-[N-(imidazo[4,5,1-de]-acridin-6-on)-aminoethylaminoethylamino-ethylamino]-4'-methyl-1'-nitroacridine×4HCl, 1-[3-(imidazo[4,5,1-de]-acridin-6-on-5-yl)aminopropyl]-4-[3'-(1'-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-1'-nitroacridine×3HCl, 9-{N-[(8-hydroxyimidazo[4,5,1-de]-acridin-6-on-5-yl)aminopropyl]-N-methylaminopropylamino}-4'-methyl-1'-nitroacridine×3HCl, 1-[3-(8-methoxy-imidazo[4,5,1-de]-acridin-6-on-5-yl)aminopropyl]-4-[3'-(1'-nitroacridin-1-yl)-aminopropyl]piperazine×4HCl, 1-[3-(imidazo[4,5,1-de]-acridin-6-on-5-yl)aminopropyl]-4-[3'-(4'-methyl-1'-nitroacridin-1-yl)-aminopropyl]piperazine×4HCl, 1-[3-(8-hydroxy-methylimidazo[4,5,1-de]-acridin-6-on-5-yl)aminopropyl]-4-[3'-(1'-nitroacridin-1-yl)-aminopropyl]piperazine×4HCl, 9-{N-[( imidazo[4,5,1-de]-acridin-6-on-5-yl)aminopropyl]-N-methylaminopropylamino}-4'-methyl-1'-nitroacridine×3HCl, 1-[3-(imidazo[4,5,1-de]-acridin-6-on-5- yl)aminopropyl]-4-[3′-(1′-nitroacridin-1-yl)-aminopropyl]piperazine×4HCl, 9-{N-[(8-hydroxyimidazo[4,5,1-de]-acridin-6-on-5-yl)aminopropyl]-N-methylaminopropylamino}-4′-methyl-1′-nitroacridine×3HCl, 9-{N-[(imidazo[4,5,1-de]-acridin-6-on-5-yl)aminopropyl]-N-methylaminopropylamino}-4′-methyl-1′-nitroacridine×3HCl, 9-{N-[(imidazo[4,5,1-de]-acridin-6-on-5-yl)aminopropyl]-N-methylaminopropylamino}-1′-nitroacridine×1.5HCl, and 9-{N-[(imidazo[4,5,1-de]-acridin-6-on-5-yl)aminopropyl]-N-methylaminopropylamino}-1′-nitroacridine×1.5HCl.